(12) United States Patent
Wilson et al.

(10) Patent No.: US 11,282,591 B2
(45) Date of Patent: Mar. 22, 2022

(54) DEVICE FOR THE CENTRALIZED MANAGEMENT OF MEDICAL TESTS AND METHODS FOR USING THE SAME

(71) Applicant: Optum, Inc., Minnetonka, MN (US)

(72) Inventors: John L. Wilson, Scottsdale, AZ (US); François Charette, Edina, MN (US)

(73) Assignee: Optum, Inc., Minnetonka, MN (US)

( * ) Notice: Subject to any disclaimer, the term of this patent is extended or adjusted under 35 U.S.C. 154(b) by 5 days.

(21) Appl. No.: 15/888,682

(22) Filed: Feb. 5, 2018

(65) Prior Publication Data

US 2019/0244687 A1 Aug. 8, 2019

(51) Int. Cl.
*G16H 10/40* (2018.01)
*G16H 10/60* (2018.01)

(52) U.S. Cl.
CPC ............ *G16H 10/40* (2018.01); *G16H 10/60* (2018.01)

(58) Field of Classification Search
CPC .............................. G16H 10/60; G06Q 40/08
See application file for complete search history.

(56) References Cited

U.S. PATENT DOCUMENTS

| | | |
|---|---|---|
| 6,306,087 B1 | 10/2001 | Barnhill et al. |
| 6,343,271 B1 | 1/2002 | Peterson et al. |
| 6,879,959 B1 | 4/2005 | Chapman et al. |
| 8,229,759 B2 | 7/2012 | Zhu et al. |
| 8,731,966 B2 | 5/2014 | Breitenstein et al. |
| 9,779,129 B1 | 10/2017 | Lequeux |
| 2002/0016923 A1 | 2/2002 | Knaus et al. |
| 2003/0229519 A1 | 12/2003 | Eidex et al. |
| 2004/0117205 A1 | 6/2004 | Reardan et al. |
| 2004/0225282 A1 | 11/2004 | Ness |
| 2006/0190295 A1 | 8/2006 | Merkin |
| 2007/0294103 A1 | 12/2007 | Ahmad et al. |
| 2008/0033751 A1 | 2/2008 | Greene |
| 2008/0120133 A1 | 5/2008 | Krishnaswami et al. |
| 2008/0147436 A1 | 6/2008 | Ohlsson |
| 2008/0288407 A1 | 11/2008 | Hamel et al. |
| 2009/0006135 A1 | 1/2009 | Keck et al. |
| 2009/0157426 A1* | 6/2009 | Malec .................... G06Q 10/10 705/3 |
| 2009/0222283 A1 | 9/2009 | Lassetter et al. |
| 2010/0152600 A1 | 6/2010 | Droitcour et al. |
| 2010/0274723 A1 | 10/2010 | Joao |
| 2011/0202370 A1* | 8/2011 | Green, III ............. G06F 19/328 705/3 |

(Continued)

OTHER PUBLICATIONS

Spend more time on care, less on billing claims and reimbursements (2017 copyright), NextGen, NextGen Clearinghouse, 6 pages, https://www.nextgen.com/eServices/Clearinghouse, Aug. 18, 2017.

(Continued)

*Primary Examiner* — Sheetal R Paulson
(74) *Attorney, Agent, or Firm* — Alston & Bird LLP

(57) ABSTRACT

Provided is a lab clearinghouse device configured to provide centralized management of medical tests across a plurality of medical providers, a plurality of lab payers, and a plurality of laboratories. The lab clearinghouse device is configured to communicate with a plurality of medical laboratories, medical providers, and lab payers to efficiently and effectively order and manage medical testing.

17 Claims, 8 Drawing Sheets

(56) References Cited

U.S. PATENT DOCUMENTS

| | | | |
|---|---|---|---|
| 2012/0029933 A1 | 2/2012 | Zubiller et al. | |
| 2012/0191471 A1* | 7/2012 | Logue | H04M 15/00 705/2 |
| 2013/0030257 A1 | 1/2013 | Nakata et al. | |
| 2013/0110755 A1 | 5/2013 | Upadhyayula et al. | |
| 2013/0173278 A1 | 7/2013 | Owings et al. | |
| 2013/0173289 A1 | 7/2013 | Owings et al. | |
| 2013/0173290 A1 | 7/2013 | Owings et al. | |
| 2014/0012599 A1 | 1/2014 | Weiss | |
| 2014/0194793 A1 | 7/2014 | Nakata et al. | |
| 2014/0222456 A1 | 8/2014 | Abou et al. | |
| 2014/0379361 A1 | 12/2014 | Mahadkar et al. | |
| 2015/0046181 A1 | 2/2015 | Adjaoute | |
| 2015/0081324 A1 | 3/2015 | Adjaoute | |
| 2015/0213225 A1 | 7/2015 | Amarasingham et al. | |
| 2015/0235334 A1 | 8/2015 | Wang et al. | |
| 2015/0278743 A1 | 10/2015 | Callas | |
| 2015/0371001 A1 | 12/2015 | Pinsonneault et al. | |
| 2016/0000515 A1 | 1/2016 | Sela et al. | |
| 2016/0110512 A1 | 4/2016 | Adjaoute | |
| 2016/0121406 A1 | 5/2016 | Weinberg | |
| 2016/0321406 A1 | 11/2016 | Timmerman et al. | |
| 2016/0321410 A1 | 11/2016 | Timmerman et al. | |
| 2016/0350498 A1 | 12/2016 | Hashoul et al. | |
| 2017/0124263 A1 | 5/2017 | Crafts, Jr. et al. | |
| 2017/0286622 A1 | 10/2017 | Cox et al. | |
| 2018/0011980 A1 | 1/2018 | Contu et al. | |
| 2018/0089781 A1* | 3/2018 | Landrum | G06Q 30/0282 |
| 2018/0096292 A1 | 4/2018 | Debusk et al. | |
| 2018/0204111 A1 | 7/2018 | Zadeh et al. | |

OTHER PUBLICATIONS

Reduction in Unnecessary Clinical Laboratory Testing Through Utilization Management at a US Government Veterans Affairs Hospital, Electronic Lab Utilization Management, Mar. 1, 2016, Konger, R. L., et al., American Journal of Pathology, pp. 355-364, 145.

Provider Payment Arrangements, Provider Risk, and Their Relationship with the Cost of Health Care, Oct. 1, 2015, Spector, Juliet M., et al., Society of Actuaries (Milliman), 91 pages.

Preventing Duplicate Laboratory Testing, May 9, 2015, Tim H, Physician's Weekly for Medical News, Journals & Articles, 4 pages, http://www.physiciansweekly.com/preventing-duplicate-laboratory-testing/, Aug. 17, 2017.

Mirth Results. Powering Health Information Exchange. (2017 Copyright), NextGen, NextGen Mirth, 4 pages, https://www.nextgen.com/lnteroperability/Mirth-Solutions, Aug. 18, 2017.

ISA/206—Invitation to Pay Additional Fees dated Apr. 12, 2018 for WO Application No. PCT/US18/016901.

IBM Counter Fraud on Cloud, (Unknown Author), 3 pages, https://www.ibm.com/bs-en/marketplace/financial-risk-and-fraud, Aug. 18, 2017.

Data Science Labs: Predictive Modeling to Detect Healthcare Fraud, Waste, and Abuse, May 9, 2013, Noah Zimmerman, Pivotal Blog, 5 pages, https://network.pivotal.io.

Contingent Payment Clauses: Enforceable? Negotiable? Worth the Risk?, Jan. 1, 2015, Matt Meaker, SacksTierney P.A., 3 pages, http://www.sackstierney.com/articles/contingent-payment-clauses.htm, Aug. 18, 2017.

International Search Report and Written Opinion for corresponding International Application No. PCT/US2018/016901, dated Jun. 11, 2018, 13 pages.

U.S. Patent and Trademark Office, Final Office Action for U.S. Appl. No. 15/888,763, filed Mar. 25, 2020, (22 pages), USA.

United States Patent and Trademark Office, NonFinal Office Action for U.S. Appl. No. 15/888,721, filed Nov. 20, 2019, (21 pages), USA.

United States Patent and Trademark Office, NonFinal Office Action for U.S. Appl. No. 15/888,763, filed Nov. 20, 2019, (33 pages), USA.

United States Patent and Trademark Office, Notice Of Allowance and Fee(s) Due for U.S. Appl. No. 15/888,721, filed Dec. 1, 2010, (40 pages), USA.

United States Patent and Trademark Office, Notice of Allowance and Fee(s) Due for U.S. Appl. No. 15/888,763, filed Jan. 14, 2021, (22 pages), USA.

* cited by examiner

DEVICE FOR THE CENTRALIZED MANAGEMENT OF MEDICAL TESTS AND METHODS FOR USING THE SAME

BACKGROUND

Laboratory medicine involves the process of capturing specimens and performing tests on the specimens. Applicant has identified a number of deficiencies and problems associated with conventional processing of medical laboratory orders and results. Through applied effort, ingenuity, and innovation, many of these identified problems have been solved by developing solutions that are included in embodiments of the present invention, many examples of which are described in detail herein.

BRIEF SUMMARY

In general, embodiments of the present invention provided herein include methods, devices, and computer program products for facilitating laboratory medicine processing.

In a first embodiment, a device is provided for centralized management of medical tests across a plurality of medical providers, a plurality of lab payers, and a plurality of laboratories, the device including a processor and a memory storing computer instructions that, when executed by the processor, cause the device to receive a lab request from a lab request initiator, the lab request initiator being associated with at least one medical provider of the plurality of medical providers, wherein the lab request includes an order for one or more medical tests to be performed; derive, using the lab request, a lab code associated with a lab fee, wherein the lab code is specific to the one or more medical tests; cause the lab request to be adjudicated; and approve or deny the lab request based on adjudicating the lab request. Approving the lab request includes transmitting the lab fee indication to one lab payer of the plurality of lab payers, generating lab instructions associated with the lab request after the lab request has been adjudicated, and transmitting the lab instructions associated with the lab request to one laboratory of the plurality of medical laboratories for performance of one or more corresponding medical tests. Denying the lab request includes transmitting a lab request denial to the lab request initiator, the lab request denial indicating that the lab request needs to be revised.

The device may further include computer instructions that, when executed by the processor, cause the device to cause the lab request to be adjudicated by causing the device to analyze patient data, physician data, provider data, laboratory data, payer data, or a combination thereof; and determine a likelihood of payment by at least one lab payer of the plurality of lab payers by comparing the patient data, physician data, provider data, lab data, payer data, or combinations thereof to the lab request. The likelihood of payment by the at least one lab payer of the plurality of lab payers may be based on a pattern of activity established in the patient data, physician data, provider data, lab data, payer data, or combinations thereof. The pattern of activity may be established in the patient data, physician data, provider data, lab data, payer data, or combinations thereof and may be based on a series of prior medical tests associated with a patient, physician, provider, laboratory, payer, or combinations thereof. The pattern of activity established in the patient data, physician data, provider data, lab data, payer data, or combinations thereof may be based on a series of prior payments made by a patient, payer, or combinations thereof. The pattern of activity established in the patient data, physician data, provider data, lab data, payer data, or combinations thereof may be based on established procedures associated with a patient, payer, or combinations thereof.

The device may further include computer instructions, when executed by the processor, further cause the device to retrieve patient data, physician data, provider data, lab data, payer data, or a combination thereof from one or more external devices operated by one or more of the plurality of medical laboratories, medical providers, lab payers, or combinations thereof. Causing the adjudication of the lab request may be based on at least a portion of the patient data, physician data, provider data, lab data, payer data, or a combination thereof retrieved from the one or more external devices.

In some embodiments, the lab request denial may include a suggested revised lab request. In some embodiments, the computer instructions, when executed by the processor, may cause the device to cause adjudication of the lab request by causing the device to translate the lab request to a lab request indication and transmit the lab request indication to a lab payer. The lab request indication may include a transmission containing information sufficient to enable the lab payer to determine a likelihood of approval of the lab request associated with the lab request indication.

In some embodiments, the computer instructions may, when executed by the processor, further cause the device to receive a lab payment indication from the at least one lab payer of the plurality of lab payers prior to generating lab instructions associated with the lab request.

In some embodiments, the computer instructions may, when executed by the processor, further cause the device to receive lab results from the at least one laboratory of the plurality of medical laboratories and transmit at least part of a lab payment to the at least one laboratory of the plurality of medical laboratories.

In some embodiments, the computer instructions may, when executed by the processor, further cause the device to transmit the lab results to the lab request initiator.

In another example embodiment, a method is provided for providing centralized management of medical tests across a plurality of medical providers, a plurality of lab payers, and a plurality of laboratories. The method may include receiving, by a lab clearinghouse circuitry, a lab request from a lab request initiator. The lab request initiator may be associated with at least one medical provider of the plurality of medical providers and the lab request may include an order for one or more medical tests to be performed. The method may also include translating, by an analytical engine, the lab request to a lab code associated with a lab fee. The lab code may be specific to the one or more medical tests. The method may also include causing, by the analytical engine, the lab request to be adjudicated and approving or denying the lab request based on adjudicating the lab request.

Approving the lab request may include transmitting, by a communications interface, the lab fee to one lab payer of the plurality of lab payers; generating, by the analytical engine, lab instructions associated with the lab request after the lab request has been adjudicated; and transmitting, by the communications interface, the lab instructions associated with the lab request to one laboratory of the plurality of medical laboratories for performance of the lab instructions. Denying the lab request may include transmitting, by the communications interface, a lab request denial to the lab request initiator, the lab request denial indicating that the lab request needs to be revised.

In some embodiments, causing the lab request to be adjudicated may include analyzing, by the analytical engine, patient data, physician data, provider data, laboratory data, payer data, or combinations thereof; and determining, by the analytical engine, a likelihood of payment by at least one lab payer of the plurality of lab payers by comparing the patient data, physician data, provider data, lab data, payer data, or combinations thereof to the lab request.

In some embodiments, the likelihood of payment by the at least one lab payer of the plurality of lab payers may be based on a pattern of activity established in the patient data, physician data, provider data, lab data, payer data, or combinations thereof. In some embodiments, the pattern of activity established in the patient data, physician data, provider data, lab data, payer data, or combinations thereof may be based on a series of prior medical tests associated with a patient, physician, provider, laboratory, payer, or combinations thereof. In some embodiments, the pattern of activity established in the patient data, physician data, provider data, lab data, payer data, or combinations thereof may be based on a series of prior payments made by a patient, payer, or combinations thereof. In some embodiments, the pattern of activity established in the patient data, physician data, provider data, lab data, payer data, or combinations thereof may be based on established procedures associated with a patient, payer, or combinations thereof.

In some embodiments, the method may further include retrieving, by the lab clearinghouse circuitry, patient data, physician data, provider data, lab data, payer data, or combinations thereof from one or more external devices operated by one or more of the plurality of medical laboratories, medical providers, lab payers, or combinations thereof. The data retrieved may be used in adjudicating the lab request.

In another example embodiments, a computer program product is provided. The computer program product may include a non-transitory computer readable medium having computer program instructions stored therein. The computer program instructions when executed by a processor may provide centralized management of medical tests across a plurality of medical providers, a plurality of lab payers, and a plurality of laboratories, by causing the computer program product to receive a lab request from a lab request initiator. The lab request initiator may be associated with at least one medical provider of the plurality of medical providers and the lab request may include an order for one or more medical tests to be performed. The computer program instructions may also cause the computer program product to translate the lab request to a lab code associated with a lab fee. The lab code may be specific to the one or more medical tests. The computer program instructions may also cause the computer program product to cause the lab request to be adjudicated and approve or deny the lab request based on adjudicating the lab request. Approving the lab request may include transmitting the lab fee to one lab payer of the plurality of lab payers, generating lab instructions associated with the lab request after the lab request has been adjudicated, and transmitting the lab instructions associated with the lab request to one laboratory of the plurality of medical laboratories for performance of the lab instructions. Denying the lab request may include transmitting a lab request denial to the lab request initiator. The lab request denial may indicate that the lab request needs to be revised.

The foregoing brief summary is provided merely for purposes of summarizing some example embodiments illustrating some aspects of the present disclosure. Accordingly, it will be appreciated that the above-described embodiments are merely examples and should not be construed to narrow the scope of the present disclosure in any way. It will be appreciated that the scope of the present disclosure encompasses many potential embodiments in addition to those summarized herein, some of which will be described in further detail below.

BRIEF DESCRIPTION OF THE FIGURES

Reference will now be made to the accompanying drawings, which are not necessarily drawn to scale, and wherein.

DETAILED DESCRIPTION

Figure 1:
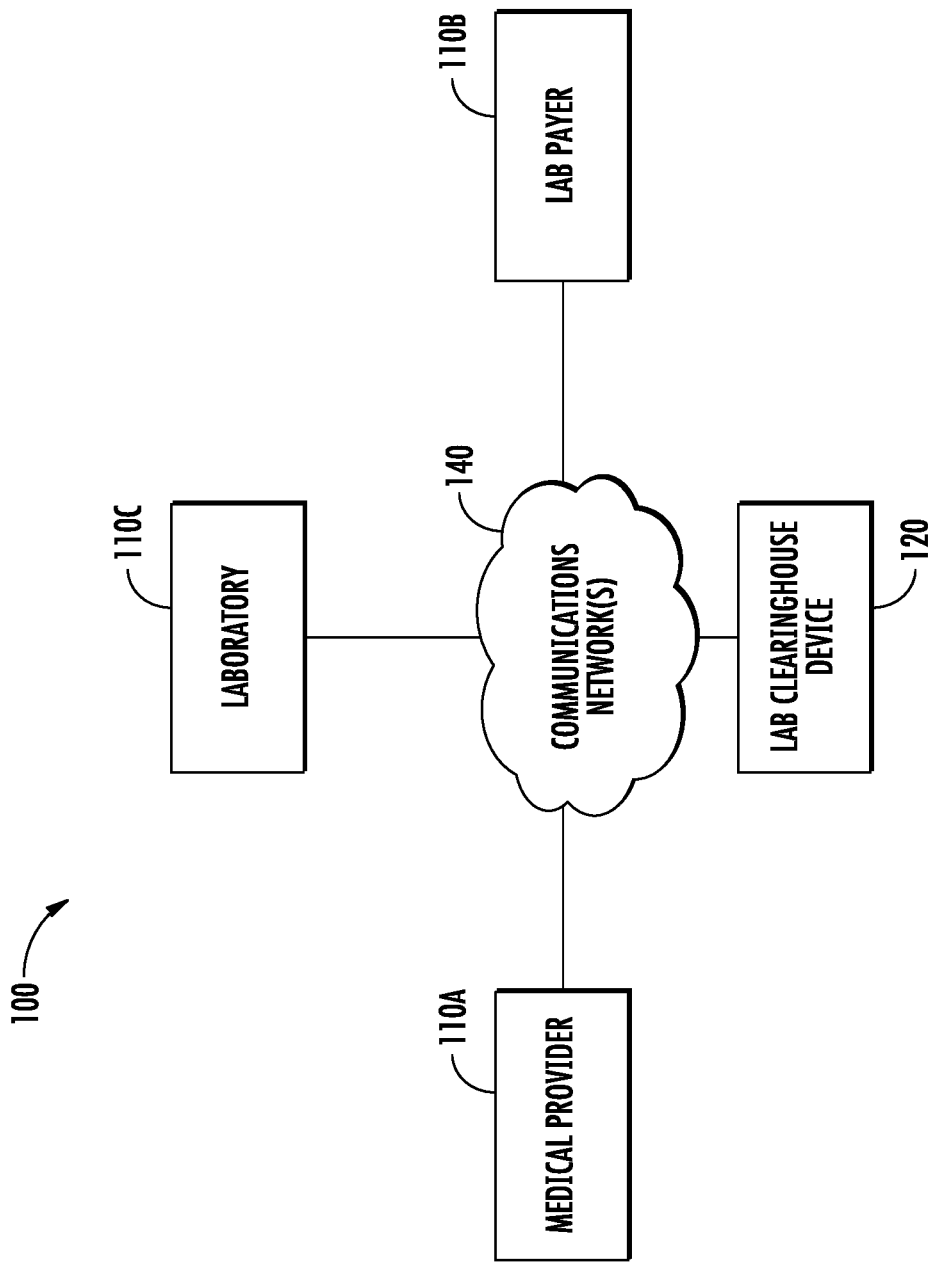
FIG. 1 illustrates an example system in accordance with some embodiments discussed herein.

Some embodiments of the present invention will now be described more fully hereinafter with reference to the accompanying drawings, in which some, but not all embodiments of the inventions are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

Terms

As used herein, the terms "data," "content," "digital content," "digital content object," "information," and similar terms may be used interchangeably to refer to data capable of being transmitted, received, and/or stored in accordance with embodiments of the present invention. Thus, use of any such terms should not be taken to limit the spirit and scope of embodiments of the present invention. Further, where a computing device is described herein to receive data from another computing device, it will be appreciated that the data may be received directly from the another computing device or may be received indirectly via one or more intermediary computing devices, such as, for example, one or more servers, relays, routers, network access points, base stations, hosts, and/or the like, sometimes referred to herein as a "network." Similarly, where a computing device is described herein to send data to another computing device, it will be appreciated that the data may be sent directly to the another computing device or may be sent indirectly via one or more intermediary computing devices, such as, for example, one or more servers, relays, routers, network access points, base stations, hosts, and/or the like.

The term "client device" refers to computer hardware and/or software that is configured to access a service made available by a server. The server is often (but not always) on another computer system, in which case the client device accesses the service by way of a network. Client devices may include, without limitation, smart phones, tablet computers, laptop computers, wearables, personal computers, enterprise computers, and the like.

The term "user" should be understood to refer to an individual, group of individuals, business, organization, and the like; the users referred to herein are accessing a group-based communication or messaging system using client devices.

The terms "profile," "account," and "account details" refer to information associated with a user (e.g., patient, provider, lab, payer, etc.), including, for example, a user identifier, an email address, a real name (e.g., John Doe), a username (e.g., jdoe), a password, a time zone, a status, and the like. The account details can include a subset designation of user credentials, such as, for example, login information for the user including the user's username and password.

As used herein, the term "profile identifier" refers to any data that identifies a user. For example, and without limitation, a profile identifier may include a unique identifier, an IP address, a MAC address, ASCII text, a pointer, a memory address and the like.

As used herein, the term "profile data" refers to any data associated with a profile identifier, such as, but not limited to, biographical data or any other data that may serve to characterize or describe the associated user.

As used herein, the term "biographical data" refers to information associated with a person(s) identified in a profile, such as, for example, birth dates, allergies, socio-economic data, place of residence, login credential information, and/or any other identifying information about a profile.

As used herein, the term "lab request" refers to any electronically generated digital content that is an instruction or direction, generally initiated by a user, for a medical test to be performed. For instance, the lab request can include an order for a medical test to be performed by a laboratory (e.g., a research or clinical laboratory). The lab request may order a specific medical test, one or more medical tests, a series of medical tests, or combinations thereof. The lab request may include an order for a specific laboratory to perform the medical test or may not specify the laboratory to perform the medical test. The lab request may include a variety of information such as identifying information regarding the patient and/or provider initiating the lab request and identifying information regarding the medical test requested.

"Lab code" refers to an identifier associating one or more medical tests ordered in a lab request with a lab fee for the one or more medical tests to be performed. A "lab code indication" refers to any electronically generated digital content that includes a lab code.

"Lab fee indication" refers to any electronically generated digital content that is an indication indicating a monetary amount identified for performance of one or more medical tests ("lab fee") ordered in a lab request.

"Lab request initiator" refers to the entity ordering the one or more medical tests listed in a lab request. The lab request initiator may be a client device operated by a physician, hospital, clinic, research facility, etc. One or more lab request initiator may be associated with a lab request. That is, a lab request may group medical tests together over more than one lab request initiator.

"Lab results" are associated with a lab request and refers to any electronically generated digital content that represent medical test results obtained from performance of one or more of the medical tests ordered in the associated lab request. "Lab results indication" refers to any electronically generated digital content that is an indication indicating that lab results have been obtained and may include the lab results. In some embodiments, the lab request indication will include the lab results. In some embodiments, particularly where the medical test was a complex test, the lab request indication may include all supporting documentation (e.g., the genomic file).

"Lab instructions" refers to any electronically generated digital content that is an indication typically provided to a laboratory (e.g., clinical or research laboratory) that sets forth one or more medical tests to be performed. The lab instructions may include a variety of information such as requested date of completion, patient data, provider data, payer data, etc. as discussed herein. In particular, the lab instructions may include any information that may help enable the receiving laboratory to perform one or more of the medical tests indicated in the lab instructions.

"Lab payment" refers to a monetary disbursement intended to compensate the direct or indirect receiver of the lab payment for performance of one or more medical tests ordered in the lab request associated with the lab payment. "Lab payment indication" refers to any electronically generated digital content that is an indication indicating that lab payment will be provided or is provided. That is, the lab payment indication may include the lab payment or indicate that payment will be provided at a later date.

"Lab request denial" is associated with a lab request and refers to any electronically generated digital content that is an indication that one or more medical tests ordered in the associated lab request should not be ordered. For instance, in some embodiments, a lab request denial may be generated in response to the determination that the associated patient's insurance policy may not or will not cover one or more medical tests ordered in the associated lab request. The lab clearinghouse device may provide the lab request denial in real-time to the lab request initiator (e.g., the ordering physician). That is, prior to execution or performance of the medical tests requested in the lab request (and prior to generation and transmission of lab instructions), the lab request may be adjudicated and a lab request denial may be generated and transmitted to the lab request initiator.

The phrase "suggested revised lab request" refers to any electronically generated digital content that is an instruction or direction, generally initiated by a user, for a medical test to be performed. The suggested revised lab request may include suggested revised medical laboratories, suggested revised medical tests, or combinations thereof that are suggested to replace or supplement the original medical laboratories or medical tests listed in a prior lab request.

"Revised lab request" refers to any electronically generated digital content that is an instruction or direction, generally initiated by a user, for a medical test to be performed and is generally generated in response to a lab request denial and is associated with a lab request. For instance, the revised lab request can include an order for one or more medical tests to be performed by a laboratory (e.g., a research or clinical laboratory). The revised lab request may order a specific medical test, one or more medical tests, a series of medical tests, or combinations thereof. The revised lab request may include an order for a specific laboratory to perform the medical test or may not be specific to the laboratory for performing the medical test. The revised lab request may include a variety of information such as identifying information regarding the patient and/or provider initiating the lab request and identifying information regarding the medical test requested.

Communications such as lab requests, lab code indication, lab fee indications, lab results, lab results indication, lab instructions, lab payment, lab payment indications, lab request denial, revised lab request, etc. may include any text, image, video, audio, or combination thereof provided by a user (using a client device). For instance, the user may provide a communication that includes text as well as an image and a video within the communication as communication contents. In such a case, the text, image, and video would comprise the communication or digital content object. Each communication sent in the lab clearinghouse system may include metadata comprising the following: a sending user identifier and communication contents. Each of the foregoing identifiers may comprise ASCII text, a pointer, a memory address, and the like.

Among the specifics listed above with regard to each type of communication (e.g., lab request, lab code indication, lab fee indications, lab results, lab results indication, lab instructions, lab payment, lab payment indications, lab request denial, revised lab request, etc.), the communications may also include information related to the user who created the communication, the client device on which the communication was first provided or is associated with, the time and date that the communication was first provided, additional communications stemming from the communication, and any other identifying information related to the communication.

A "sending user identifier" is associated with a communication that is sent by a particular user (i.e., a client device associated with the particular user). The sending user identifier may be analyzed to determine context regarding the user (e.g., patterns associated with the user).

Overview

Various embodiments of the invention are directed to systems, methods, devices, and computer program products that are configured to efficiently process laboratory orders, results, and payments within a defined system across medical laboratories, lab payers, and medical providers.

Provided herein are systems, methods, devices, and computer program products to manage lab requests and lab payments. To facilitate this process, a lab clearinghouse device is designed to be the intermediary in transmissions between patients, providers (e.g., physicians, hospitals, etc.), lab payers, and laboratories, and as a result, the lab clearinghouse device has access to information, e.g., electronic medical records, from each of these entities. The lab clearinghouse device may provide real-time decision support integrations with the ordering provider (e.g., individual physician, physician group, hospital) workflow and may provide real-time adjudication of a lab request. The lab clearinghouse device may adjudicate the lab request in real-time based on information received from the provider, the member (e.g., patient), the lab payer, and any contract with the lab to perform the medical tests ordered in the lab request. By adjudicating lab requests in advance of ordering lab work, the lab clearinghouse device will eliminate the need for laboratories to create insurance claims for payment, or for lab payers to adjudicate such insurance claims. The lab clearinghouse device may generate a lab fee indication indicating that payment for one or more medical tests is needed. Payment of the medical tests may be requested, agreed to, and may be required prior to the lab clearinghouse device initiating transmission of lab instructions for performance of the medical tests by a lab. Through the use of a lab clearinghouse device as described herein, lab payers and laboratories may realize reduced costs and increased efficiency due to the removal of the need to create insurance claims. Similarly, through the use of a lab clearinghouse device as described herein, lab payers and medical providers may have access to data (e.g., detailed and complex test results) through the lab clearinghouse device that may otherwise not be readily accessible.

Laboratories may experience an increase in revenue due to the payment of lab payer liability (e.g., member liability) prior to performance of the medical tests and may have less administrative costs due to the removal of the claims processing system. High-deductible health plans are increasing in popularity. These plans place more liability on the patient. Such liability is difficult and costly for the laboratories to track down and successfully obtain. However, through the use of a lab clearinghouse device as described herein, liability is established and resolved prior to performance of the medical tests by the laboratory. By conditioning performance of the laboratory work on payment or agreement to payment, laboratories may experience an increase in payments received and a concomitant decrease in the overhead associated with debt collection.

The lab clearinghouse device may be able to communicate with electronic medical records (e.g., HL7 ORU (results) and REST API), with billing systems (e.g., payments (EFT/checks)) for on-premise laboratories, payers (e.g., invoices and encounters, pre-authorization EDI 278), and laboratories (e.g., HL7 OBM (order) and HL7 ORU (results), and payments (EFT/checks)).

The lab clearinghouse device allows for shifting of the price structure away from claims-based payment adjudication that prices large groups of tests under broad claims to a model that prices medical tests based on the individual requirements of the medical tests themselves. Specifically, medical tests may be priced based on the underlying data regarding the lab request (e.g., patient, laboratory, etc.) rather than the insurance claim that results from a lab request. With this more granular pricing structure, use of a lab clearinghouse device as described herein enables medical tests to be priced based on the actual needs of the patient. Further, with the use of the lab clearinghouse device, denial of payment by insurance companies due to ineligible tests, clinical editing, duplicate tests, etc. can be avoided on the front end.

The lab clearinghouse device may be configured to adjudicate lab requests (e.g., analysis, approval/denial, payment, etc.) and provide relevant information to the appropriate parties (e.g., laboratories, payers, medical providers, etc.) efficiently and effectively. The manner by which the lab clearinghouse device provides adjudication of lab requests is rooted in computer technology in order to overcome a problem specifically arising in the realm of computer networks. Specifically, current systems for adjudicating payment of lab requests operates in a disjointed fashion in which various component nodes within an interconnected system (i.e., medical providers, laboratories, and payers such as insurance companies) have access to different subsets of information. Producing gains in efficiency, speed, or resource allocation thus requires these entities to employ sophisticated software and computer tools to account for the information not known to them a priori. For instance, a medical provider is able to determine what medical tests may be required to provide appropriate care to a given patient, but is often unable to determine whether the medical test would be covered by the patient's insurance carrier. Similarly, a laboratory may be unable to determine whether the requested medical tests are covered by the patient's insurance, and may thus be forced to employ sophisticated software tools to evaluate the patient's ability to pay for the medical tests should the insurer not cover it. Finally, insurance companies may not have access to the requested medical tests and rather, simply see the resulting claims, and may thus be forced to employ sophisticated software tools to evaluate whether the claims are covered by the patient's policy. Through the use of a lab clearinghouse system employing the lab clearinghouse device, all of this technical complexity can be avoided by centralizing the collection of data from these various entities into a single lab clearinghouse device. Accordingly, the lab clearinghouse device may allow for less strain on the systems of the medical providers, laboratories, and lab payers leading to increased system efficiency. Due to the removal of the need to create and submit claims, this effect is particularly amplified for laboratories and lab payers. The lab clearinghouse device may also allow for reduced network traffic and data processing on the part of the various entities with which it interacts by removing the need to create and submit claims (e.g., intermediary systems, collection agencies, and the like). Moreover, medical tests may be priced more specifically (rather than being grouped with 100's of other labs and priced with those other labs), thereby reducing costs for the lab payer and the patient (e.g., due to reduced denials). The lab clearinghouse device may also increase provider engagement as the provider communicates with the lab clearinghouse device to determine the lab request (e.g., through suggested revised lab requests and revised lab requests).

Previously, patients may have had difficulty accessing lab results. However, through the use of a lab clearinghouse system predicated on a lab clearinghouse device, patients may receive lab results via the lab clearinghouse device, directly or indirectly, and may no longer need to track down lab results from laboratories directly.

The lab clearinghouse device may be used as part of a standalone service, application, or device or it may be applied as a layer atop an existing service application or device.

Example System Architecture

Methods, devices, and computer program products of the present invention may be embodied by any of a variety of devices. For example, the method, device, and computer program product of an example embodiment may be embodied by a networked device (e.g., an enterprise platform), such as a server or other network entity, configured to communicate with one or more devices, such as one or more client devices. Additionally or alternatively, the computing device may include fixed computing devices, such as a personal computer or a computer workstation. Still further, example embodiments may be embodied by any of a variety of mobile devices, such as a portable digital assistant (PDA), mobile telephone, smartphone, laptop computer, tablet computer, wearable, or any combination of the aforementioned devices.

FIG. 1 shows lab clearinghouse system 100 including an example network architecture for a system, which may include one or more devices and sub-systems that are configured to implement some embodiments discussed herein. For example, lab clearinghouse system 100 may include lab clearinghouse device 120, which can include, for example, the circuitry disclosed in FIGS. 2-4, one or more client devices, one or more servers, or database, among other things (not shown). The lab clearinghouse device 120 may include any suitable network server and/or other type of processing device. In some embodiments, the lab clearinghouse device 120 may receive lab requests, revised lab requests, lab payments, etc. and generate and transmit lab instructions, lab fee indications, lab code indications, suggested revised lab requests, etc. to external devices such as one or more medical providers 110A, laboratories 110C, and lab payers 110B using data from the lab clearinghouse data store 300 (see e.g., FIG. 2). The lab clearinghouse data store 300 may be embodied as a data storage device such as a Network Attached Storage (NAS) device or devices, as a separate database server or servers (e.g., cloud computing), or distributed across multiple devices in a network (e.g., blockchain). The lab clearinghouse data store 300 stores information for the lab clearinghouse device 120 to facilitate the operations of the lab clearinghouse system 100. For example, the lab clearinghouse data store 300 may include, without limitation, a plurality of data regarding patients, medical tests, laboratories, medical providers, lab payers, etc., organized within the lab clearinghouse data store 300.

Lab clearinghouse device 120 can communicate with one or more medical providers 110A, laboratories 110C, and lab payers 110B, each of which may include one or more client devices and/or servers, via network 140. In this regard, network 140 may include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, etc.). For example, network 140 may include a cellular telephone, an 802.11, 802.16, 802.20, and/or WiMax network. Further, the network 140 may include a public network, such as the Internet, a private network, such as an intranet, or combinations thereof, and may utilize a variety of networking protocols now available or later developed including, but not limited to TCP/IP based networking protocols. For instance, the networking protocol may be customized to suit the needs of the lab clearinghouse device 120 and/or lab clearinghouse system 100.

The lab clearinghouse device 120 may provide for receiving of electronic data from various sources, including but not necessarily limited to one or more medical providers 110A, laboratories 110C, and lab payers 110B, via for instance client devices or servers within the one or more medical providers 110A, laboratories 110C, and lab payers 110B. For example, the lab clearinghouse device 120 may be operable to receive and post or transmit communications provided by the one or more medical providers 110A, laboratories 110C, and lab payers 110B.

Lab clearinghouse device 120, medical providers 110A, laboratories 110C, and lab payers 110B may each be implemented as a personal computer and/or other networked device, such as a cellular phone, tablet computer, mobile device, desktop computer, laptop computer, smartphone, netbook, wearable, and the like, that may be used for any suitable purpose in addition to processing lab requests, lab results, and lab payments etc. The depiction in FIG. 1 of one medical provider 110A, one lab payer 110B, and one laboratory 110C is merely for illustration purposes. Any number of medical providers 110A, lab payers 110B, and laboratories 110C may be included in the lab clearinghouse system 100. In one embodiment, the medical providers 110A, lab payers 110B, and laboratories 110C may be configured to display an interface on a display of the respective device for viewing, creating, editing, and/or otherwise interacting with lab clearinghouse device 120. According to some embodiments, the lab clearinghouse device 120 may be configured to display an interface on a display of the lab clearinghouse device 120 for viewing, creating, editing, and/or otherwise interacting with the medical providers 110A, lab payers 110B, and laboratories 110C. In some embodiments, an interface of a medical provider 110A, lab payer 110B, and laboratory 110C may be the same or different from an interface of a lab clearinghouse device 120. Lab clearinghouse system 100 may also include additional client devices and/or servers, among other things. Additionally or alternatively, the lab clearinghouse device 120, medical providers 110A, lab payers 110B, and laboratories 110C may interact within the lab clearinghouse system 100 via a web browser. As yet another example, the lab clearinghouse device 120, medical providers 110A, lab payers 110B, and laboratories 110C may include various hardware or firmware designed to interface with the various other devices within the lab clearinghouse system 100.

The lab clearinghouse device 120, medical providers 110A, lab payers 110B, and laboratories 110C may be any computing device as defined above. Electronic data received by the lab clearinghouse device 120 from the medical providers 110A, lab payers 110B, and laboratories 110C may be provided in various forms and via various methods. Electronic data received by the medical providers 110A, lab payers 110B, and laboratories 110C from the lab clearinghouse device 120 may be provided in various forms and via various methods. For example, the lab clearinghouse device may be able to communicate with electronic medical records (e.g., HL7 ORU (results) and REST API), with billing systems (e.g., payments (EFT/checks)) for on-premise laboratories, payers (e.g., invoices and encounters, pre-authorization EDI 278), and laboratories (e.g., HL7 OBM (order) and HL7 ORU (results), and payments (EFT/checks)).

In embodiments where any of the lab clearinghouse device 120, medical provider 110A, lab payer 110B, and laboratory 110C is a mobile device, such as a smart phone or tablet, the respective client device may execute an "app" to operate within the lab clearinghouse system 100. Such apps are typically designed to execute on mobile devices, such as tablets or smartphones. For example, an app may be provided that executes on mobile device operating systems such as iOS®, Android®, or Windows®. These platforms typically provide frameworks that allow apps to communicate with one another and with particular hardware and software components of mobile devices. For example, the mobile operating systems named above each provide frameworks for interacting with location services circuitry, wired and wireless network interfaces, user contacts, and other applications. Communication with hardware and software modules executing outside of the app is typically provided via application programming interfaces (APIs) provided by the mobile device operating system.

Additionally or alternatively, the lab clearinghouse device 120, medical provider 110A, lab payer 110B, and laboratory 110C may interact with other devices within the lab clearinghouse system 100 via a web browser.

In some embodiments of an exemplary system, a communication (e.g., a lab request, lab instructions, lab fee indication, lab payment indication, lab request denial, patient data, provider data, physician data, payer data, etc.) may be sent from a medical provider 110A, lab payer 110B, and/or laboratory 110C to a lab clearinghouse device 120. In various implementations, the communication may be sent directly to the lab clearinghouse device 120 (e.g., via a peer-to-peer connection) or over a network 140, in which case the communication may in some embodiments be transmitted via an intermediary such as a message server, and/or the like. In one implementation, the communication may include data such as a sending user identifier, communication contents (e.g., text, emojis, images, links), attachments (e.g., files), communication hierarchy data (e.g., whether the communication is a reply to another communication), metadata, and/or the like.

The lab clearinghouse system 100 may include a server (e.g., as part of the lab clearinghouse device 120) that may store communications, which may be indexed, in a lab clearinghouse data store 300. In some embodiments, a storage communication may be generated and stored in remote storage (e.g., cloud storage). In one implementation, the storage communication may include data such as a sending user identifier, communication contents, attachments, message hierarchy data, metadata, and/or the like.

In one implementation, the communication may be parsed by the lab clearinghouse device 120 to identify various components included therein. Parsing of the communication may facilitate determination by the lab clearinghouse device 120 of a sending user identifier of the user who sent the message and/or to the contents of the communication and to what or whom the communication relates. Similarly, parsing of the communication enables the lab clearinghouse device 120 to determine topics discussed in the message (e.g., medical tests, lab results, lab payments, lab codes, lab fees, etc.). In another example, the communication may be analyzed (e.g., by itself, or with other communications) or parsed using a machine learning technique, such as topic modeling, to determine topics associated with the message. The topics may help provide context for the communication such that the lab clearinghouse device 120 and other components of the lab clearinghouse system 100 may generate an appropriate response.

In some embodiments, attachments may be included with the communication. If there are attachments, files may be associated with the communication. In one implementation, the communication may be parsed to determine information regarding the attachments, such as file names and contents, which may in turn be analyzed to determine the context of the communication (e.g., to determine whether the communication relates to a lab fee, lab payment, lab results, etc.).

In embodiments, metadata may be associated with the communication. For example, metadata may provide additional context regarding the communication or the user that is specific to a company, organization, and/or the like. In one implementation, the communication may be parsed to determine metadata. For example, metadata may provide data regarding the user who sent the communication.

In embodiments, various metadata, determined as described above, and/or the contents of the communication may be used to index the communication to facilitate various facets of searching (i.e., search queries that return results from lab clearinghouse data store 300). In one implementation, a communication may be sent from lab clearinghouse device 120 to facilitate indexing in the lab clearinghouse data store 300. In another implementation, metadata associated with the communication may be determined and the communication may be indexed in the lab clearinghouse data store 300. In one embodiment, the communication may be indexed such that a company's or an organization's communications are indexed separately (e.g., in a separate index associated with the organization and/or company that is not shared with other organizations and/or companies). In one implementation, communications may be indexed at a separate distributed database (e.g., to facilitate data isolation for security purposes).

If there are attachments associated with the communication, file contents of the associated files may be used to index such files in the lab clearinghouse data store 300 to facilitate searching. In one embodiment, the files may be indexed such that a company's or an organization's files are indexed at a separate distributed database.

Figure 2:
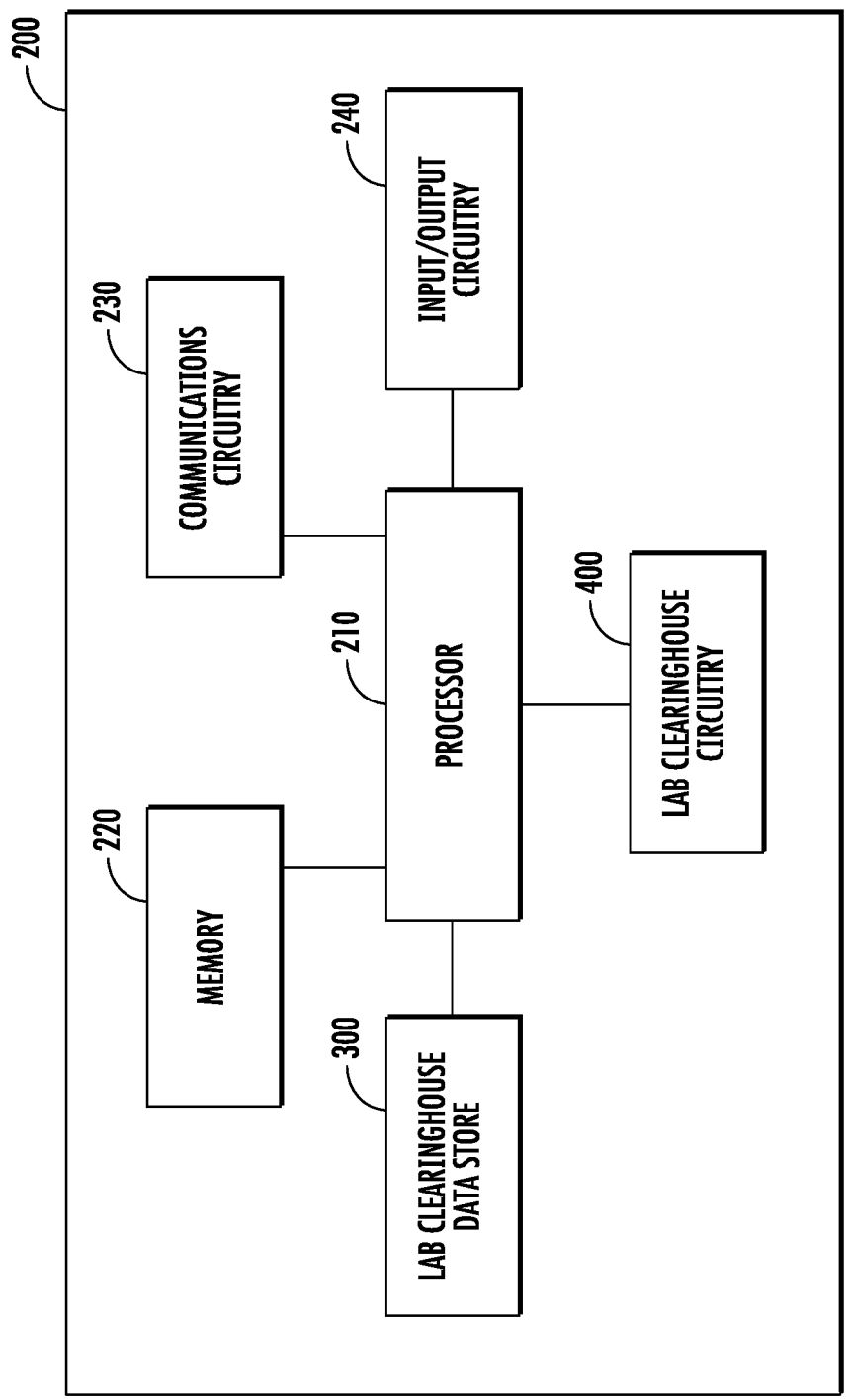
FIG. 2 illustrates a schematic block diagram of circuitry that can be included in a computing device in accordance with some embodiments discussed herein.
Figure 3:
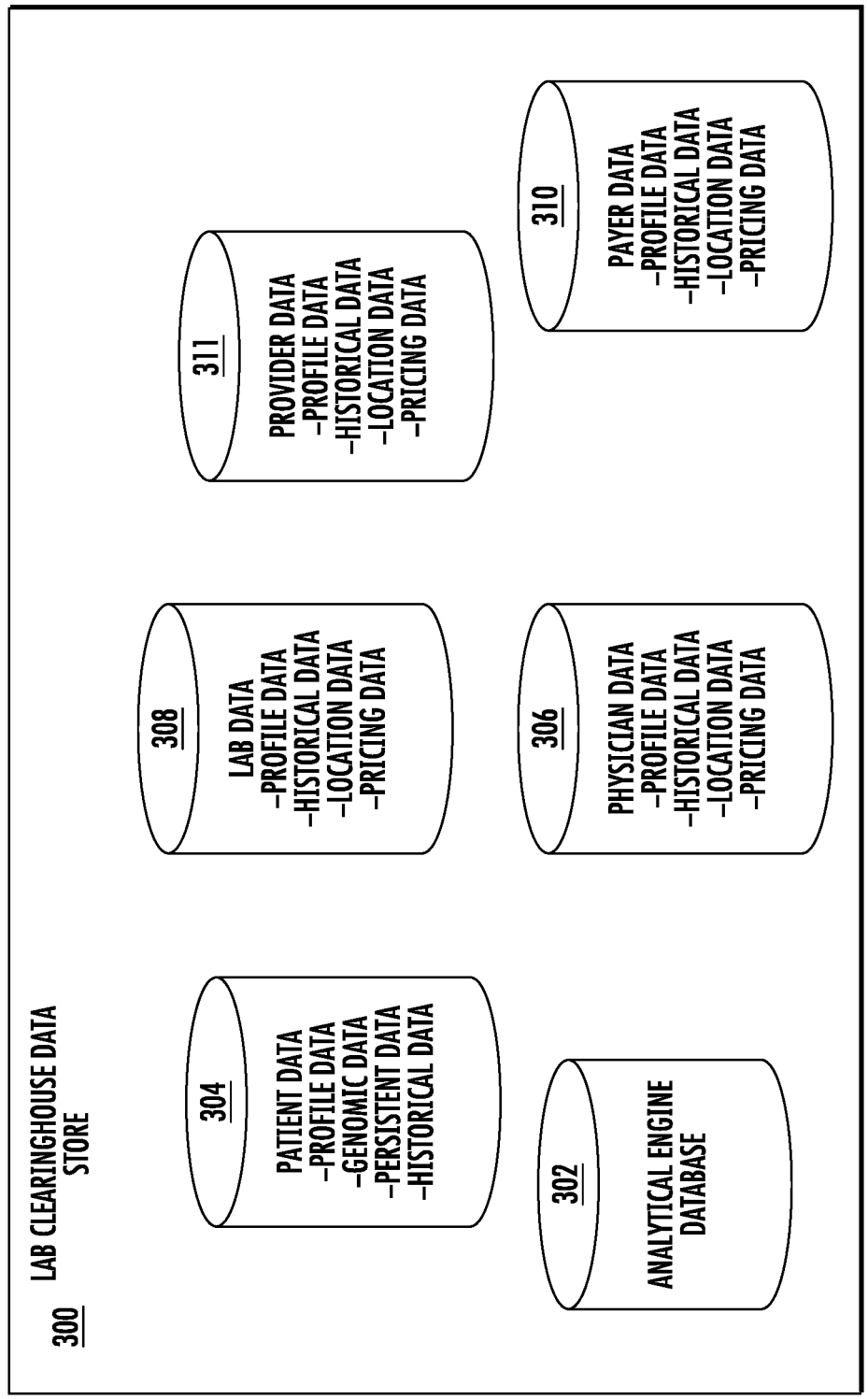
FIG. 3 illustrates an example lab clearinghouse data store in accordance with some embodiments discussed herein.

FIG. 2 shows a schematic block diagram of an apparatus 200, some or all of the components of which may be included, in various embodiments, in lab clearinghouse device 120 and/or medical provider 110A, lab payer 110B, and laboratory 110C. Any of the aforementioned systems or devices may include the components of the apparatus 200 and may be configured to, either independently or jointly with other devices in a lab clearinghouse system 100, to perform the functions of the apparatus 200 described herein. As illustrated in FIG. 2, in accordance with some example embodiments, apparatus 200 can includes various means, such as processor 210, memory 220, communications circuitry 230, and/or input/output circuitry 240. In some embodiments, lab clearinghouse data store 300 and/or lab clearinghouse circuitry 400 may also or instead be included. As referred to herein, "circuitry" includes hardware, or a combination of hardware with software configured to perform one or more particular functions. In this regard, the various components of apparatus 200 described herein may be embodied as, for example, circuitry, hardware elements (e.g., a suitably programmed processor, combinational logic circuit, and/or the like), a computer program product comprising computer-readable program instructions stored on a non-transitory computer-readable medium (e.g., memory 220) that is executable by a suitably configured processing device (e.g., processor 210), or some combination thereof. In some embodiments, one or more of these circuitries may be hosted remotely (e.g., by one or more separate devices or one or more cloud servers) and thus need not reside on the data set device or user device. The functionality of one or more of these circuitries may be distributed across multiple computers across a network.

Processor 210 may, for example, be embodied as various means including one or more microprocessors with accompanying digital signal processor(s), one or more processor(s) without an accompanying digital signal processor, one or more coprocessors, one or more multi-core processors, one or more controllers, processing circuitry, one or more computers, various other processing elements including integrated circuits such as, for example, an ASIC (application specific integrated circuit) or FPGA (field programmable gate array), or some combination thereof. Accordingly, although illustrated in FIG. 2 as a single processor, in some embodiments processor 210 comprises a plurality of processors. The plurality of processors may be embodied on a single computing device or may be distributed across a plurality of computing devices collectively configured to function as apparatus 200. The plurality of processors may be in operative communication with each other and may be collectively configured to perform one or more functionalities of apparatus 200 as described herein. In an example embodiment, processor 210 is configured to execute instructions stored in memory 220 or otherwise accessible to processor 210. These instructions, when executed by processor 210, may cause the apparatus 200 to perform one or more of the functionalities described herein.

Whether configured by hardware, or a combination of hardware with firmware/software methods, processor 210 may comprise an entity capable of performing operations according to embodiments of the present invention while configured accordingly. Thus, for example, when processor 210 is embodied as an ASIC, FPGA or the like, processor 210 may comprise the specifically configured hardware for conducting one or more operations described herein. Alternatively, as another example, when processor 210 is embodied as an executor of instructions, such as may be stored in memory 220, the instructions may specifically configure processor 210 to perform one or more algorithms and operations described herein, such as those discussed in connection with FIGS. 5-8.

Memory 220 may comprise, for example, volatile memory, non-volatile memory, or some combination thereof. Although illustrated in FIG. 2 as a single memory, memory 220 may comprise a plurality of memory components. The plurality of memory components may be embodied on a single computing device or distributed across a plurality of computing devices. In various embodiments, memory 220 may comprise, for example, a hard disk, random access memory, cache memory, flash memory, a compact disc read only memory (CD-ROM), digital versatile disc read only memory (DVD-ROM), an optical disc, circuitry configured to store information, or some combination thereof. Memory 220 may be configured to store information, data (including item data and/or profile data), applications, instructions, or the like for enabling apparatus 200 to carry out various functions in accordance with example embodiments of the present invention. For example, in at least some embodiments, memory 220 is configured to buffer input data for processing by processor 210. Additionally or alternatively, in at least some embodiments, memory 220 is configured to store program instructions for execution by processor 210. Memory 220 may store information in the form of static and/or dynamic information. This stored information may be stored and/or used by the apparatus 200 during the course of performing its functionalities.

Communications circuitry 230 may be embodied as any device or means embodied in circuitry, hardware, a computer program product comprising computer readable program instructions stored on a computer readable medium (e.g., memory 220) and executed by a processing device (e.g., processor 210), or a combination thereof that is configured to receive and/or transmit data from/to another device and/or network, such as, for example, a second apparatus 200 and/or the like. In some embodiments, communications circuitry 230 (like other components discussed herein) can be at least partially embodied as or otherwise controlled by processor 210. In this regard, communications circuitry 230 may be in communication with processor 210, such as via a bus. Communications circuitry 230 may include, for example, an antenna, a transmitter, a receiver, a transceiver, network interface card and/or supporting hardware and/or firmware/software for enabling communications with another computing device. Communications circuitry 230 may be configured to receive and/or transmit any data that may be stored by memory 220 using any protocol that may be used for communications between computing devices. Communications circuitry 230 may additionally or alternatively be in communication with the memory 220, input/output circuitry 240 and/or any other component of apparatus 200, such as via a bus.

Input/output circuitry 240 may be in communication with processor 210 to receive an indication of a user input and/or to provide an audible, visual, mechanical, or other output to a user (e.g., provider and/or consumer). Some example visual outputs that may be provided to a user by apparatus 200 are discussed in connection with FIGS. 5-8. As such, input/output circuitry 240 may include support, for example, for a keyboard, a mouse, a joystick, a display, a touch screen display, a microphone, a speaker, a RFID reader, barcode reader, biometric scanner, and/or other input/output mechanisms. In embodiments wherein apparatus 200 is embodied as a server or database, aspects of input/output circuitry 240 may be reduced as compared to embodiments where apparatus 200 is implemented as an end-user machine (e.g., lab payer device and/or provider device) or other type of device designed for complex user interactions. In some embodiments (like other components discussed herein), input/output circuitry 240 may even be eliminated from apparatus 200. Alternatively, such as in embodiments wherein apparatus 200 is embodied as a server or database, at least some aspects of input/output circuitry 240 may be embodied on an apparatus used by a user that is in communication with apparatus 200. Input/output circuitry 240 may be in communication with the memory 220, communications circuitry 230, and/or any other component(s), such as via a bus. One or more than one input/output circuitry and/or other component can be included in apparatus 200.

Lab clearinghouse data store 300 and lab clearinghouse circuitry 400 may also or instead be included and configured to perform the functionality discussed herein related to storing, generating, and/or editing communications. In some embodiments, some or all of the functionality of these components of the apparatus 200 may be performed by processor 210, although in some embodiments, these components may include distinct hardware circuitry designed to perform their respective functions. In this regard, the example processes and algorithms discussed herein can be performed by at least one processor 210, lab clearinghouse data store 300, and/or lab clearinghouse circuitry 400. For example, non-transitory computer readable media can be configured to store firmware, one or more application programs, and/or other software, which include instructions and other computer-readable program code portions that can be executed to control each processor (e.g., processor 210, lab clearinghouse data store 300, and lab clearinghouse circuitry 400) of the components of apparatus 200 to implement various operations, including the examples shown above. As such, a series of computer-readable program code portions are embodied in one or more computer program goods and can be used, with a computing device, server, and/or other programmable apparatus, to produce machine-implemented processes.

In some embodiments, the lab clearinghouse data store 300 may store patient data 304, lab data 308, physician data 306, payer data 310, provider data 311, and/or analytical engine data 302. Patient data 304 may include various information, such as profile data (e.g., biological data, preference data, name, address, contact information, insurance provider, etc.), genomic data (e.g., genomic test results), persistent data (e.g., sex, birthdate, etc.), historical data (e.g., past disease conditions, medical tests and results, surgeries, family medical data, etc.) particular to the patient (e.g., regardless of the medical provider, laboratory, and lab payer). This data may be retrieved from any of a variety of sources, such as from any of a number of medical providers 110A, lab payers 110B, or laboratories 110C, from a patient via a separate patient terminal (not shown in FIG. 1), or from any of a number of other third party devices that may be connected to the lab clearinghouse device 120. Lab data 308 may include various information, such as profile data (e.g., preference data, name, address, contact information, etc.), historical data (e.g., prior labs performed, etc.), location data (e.g., region, state, etc.), and pricing data (e.g., current pricing structure, past pricing structure, etc.) particular to a laboratory (e.g., regardless of the medical provider, patient, and lab payer). This data may most likely be retrieved from the laboratory to which it relates, although in some embodiments this data may also be retrieved from other sources who interact with the laboratory and thus acquire information regarding the various practices of the laboratory. Provider data 311 may include various information, such as profile data (e.g., preference data, name, address, contact information, etc.), historical data (e.g., prior labs requested, etc.), location data (e.g., region, state, etc.), and pricing data (e.g., current pricing structure, past pricing structure, etc.) particular to the medical provider (e.g., regardless of the patient, laboratory, and lab payer). As with the patient data 304 and laboratory data 308, this provider data 311 may be retrieved from a wide variety of sources, such as any of the devices that may interact with the lab clearinghouse 120. Finally, through similar sources, the lab clearinghouse data store 300 may acquire and store physician data 306, which may be more specific to individual physicians (rather than a group of physicians which may be referred to as a single provider) and may include various information, such as profile data (e.g., preference data, name, address, contact information, etc.), historical data (e.g., prior labs requested, etc.), location data (e.g., region, state, etc.), and pricing data (e.g., current pricing structure, past pricing structure, etc.) particular to the physician (e.g., regardless of the medical provider (e.g., hospital or physician group), patient, laboratory, and lab payer), and payer data 310, which may include various information, such as profile data (e.g., preference data, name, address, contact information, etc.), historical data (e.g., prior payments, prior policies, etc.), location data (e.g., region, state, etc.), and pricing data (e.g., current pricing structure, past pricing structure, etc.) particular to a lab payer (e.g., regardless of the provider, patient, and laboratory). Additionally or alternatively, the lab clearinghouse data store 300 may include analytical engine data 302 which provides any additional information needed by the processor 210 in analyzing and generating communications.

Overlap among the data obtained by the lab clearinghouse data store 300 among the patient data 304, lab data 308, physician data 306, payer data 310, provider data 311, and/or analytical engine data 302 may occur and information from one or more of these databases may be retrieved from the medical provider 110A, lab payer 110B, and laboratory 110C to support the lab clearinghouse circuitry 400.

Lab clearinghouse circuitry 400 can be configured to analyze multiple sets of requests, indications, lab payments, lab fees, data, other communications discussed herein and combinations thereof, such as any combination of the data in the lab clearinghouse data store 300. In this way, lab clearinghouse circuitry 400 may execute multiple algorithms, including those discussed below with respect to the lab clearinghouse system 100.

Figure 4:
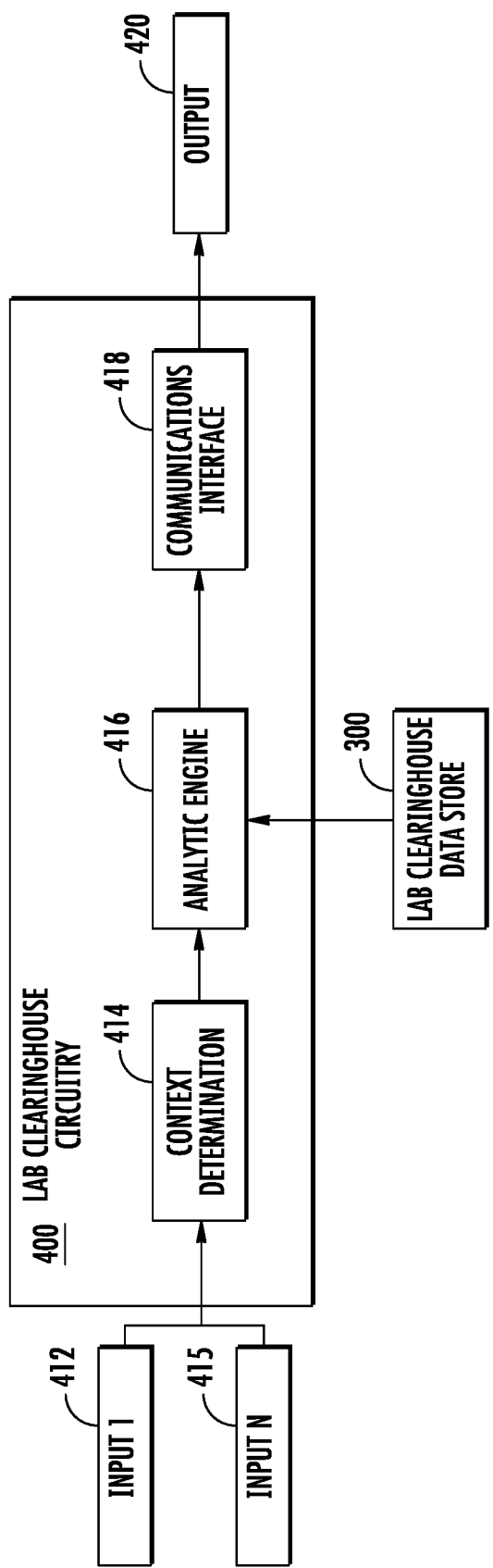
FIG. 4 illustrates example lab clearinghouse circuitry in accordance with some embodiments discussed herein.

In some embodiments, with reference to FIG. 4, the lab clearinghouse circuitry 400 may include a context determination module 414, an analytical engine 416, and communications interface 418, all of which may be in communication with the lab clearinghouse data store 300. In some embodiments, the context determination module 414 may be implemented using one or more of the components of apparatus 200. For instance, the context determination module 414 may be implemented using one or more of the processor 210, memory 220, communications circuitry 230, and input/output circuitry 240. For instance, the context determination module 414 may be implemented using one or more of the processor 210 and memory 220. The analytical engine 416 may be implemented using one or more of the processor 210, memory 220, communications circuitry 230, and input/output circuitry 240. For instance, the analytical engine 416 may be implemented using one or more of the processor 210 and memory 220. The communications interface 418 may be implemented using one or more of the processor 210, memory 220, communications circuitry 230, and input/output circuitry 240. For instance, the communications interface 418 may be implemented using one or more of the communications circuitry 230 and input/output circuitry 240.

The lab clearinghouse circuitry 400 may receive one or more communications (e.g., lab requests, lab payments, lab results indications, revised lab requests, etc.) and may generate the appropriate communications (e.g., lab fee indication, lab instructions, lab request denial, suggested revised lab request, etc.) in response. The lab clearinghouse circuitry 400 may use any of the algorithms or processes disclosed herein for receiving any of the requests, indications, payments, fees, data, etc. discussed herein and generating the appropriate communications and/or data in response. In some other embodiments, such as when the apparatus 200 is embodied in a server and/or client devices, the lab clearinghouse circuitry 400 may be located in another apparatus 200 or another device, such as another server and/or client devices.

The lab clearinghouse circuitry 400 can be configured to access data corresponding to multiple medical providers 110A, lab payers 110B, laboratories 110C, patients, etc., and generate one or more appropriate requests, indications, lab fees, lab payments, data, and/or other communications in response.

The system may receive a plurality of inputs 412, 415 from the apparatus 200 and process the inputs within the lab clearinghouse circuitry 400 to produce an output 420, which may include appropriate requests, indications, lab fees, lab payments, data, and/or other communications in response. In some embodiments, the lab clearinghouse circuitry 400 may execute context determination using the context determination module 414, process the communication and/or data in an analytical engine 416, and output the results via a communications interface 418. Each of these steps may retrieve data from a variety of sources including the lab clearinghouse data store 300.

When inputs 412, 415 are received by the lab clearinghouse circuitry 400, the context determination module 414 may make a context determination regarding the communication. A context determination includes such information as a user preference data, when and what user initiated generation of the input (e.g., when and who selected the actuator that initiated the lab request), what type of input was provided (e.g., was a lab request initiated or a revised lab request initiated) and under what circumstances receipt of the input was initiated (e.g., patient data, provider data, etc. related to the input). This information may give context to the lab clearinghouse circuitry 400 for subsequent determinations. For example, the context determination module 414 may inform the lab clearinghouse circuitry 400 as to the communication content to output with a communication.

The lab clearinghouse circuitry 400 may then compute the output using the analytical engine 416. The analytical engine 416 draws the applicable data from the lab clearinghouse data store 300 and then, based on the context determination made by the context determination module 414, computes an output, which may vary based on the input. The communications interface 418 then outputs the output 420 to the apparatus 200 for display on the appropriate device. For instance, the context determination module 414 may determine that a lab request was received from a medical provider 110A. Based on this information as well as the applicable data from the lab clearinghouse data store 300 (e.g., patient data, provider data, payer data, etc.), the analytical engine 416 may determine an appropriate output 420, such as whether a lab request denial should be generated and transmitted to the lab request initiator, whether a lab fee indication should be generated and transmitted to a lab payer 110B, or whether lab instructions should be generated and transmitted to a laboratory 110C. The analytical engine 416 may also determine that certain data in the lab clearinghouse data store 300 should be updated to reflect the new information contained in the received input. Similarly, the context determination module 414 may determine that a revised lab request, lab payment, lab results indication, or the like was received, and may further determine whether any additional contextual information was received, and the analytical engine 416 may determine the appropriate output based on this information as well as additional information from the lab clearinghouse data store 300, as further described herein.

As will be appreciated, any such computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

It is also noted that all or some of the information presented by the example devices and systems discussed herein can be based on data that is received, generated and/or maintained by one or more components of a local or networked system and/or apparatus 200. In some embodiments, one or more external systems (such as a remote cloud computing and/or data storage system) may also be leveraged to provide at least some of the functionality discussed herein.

As described above and as will be appreciated based on this disclosure, embodiments of the present invention may be configured as methods, personal computers, servers, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Example Operations of the Lab Clearinghouse System

Figure 5:
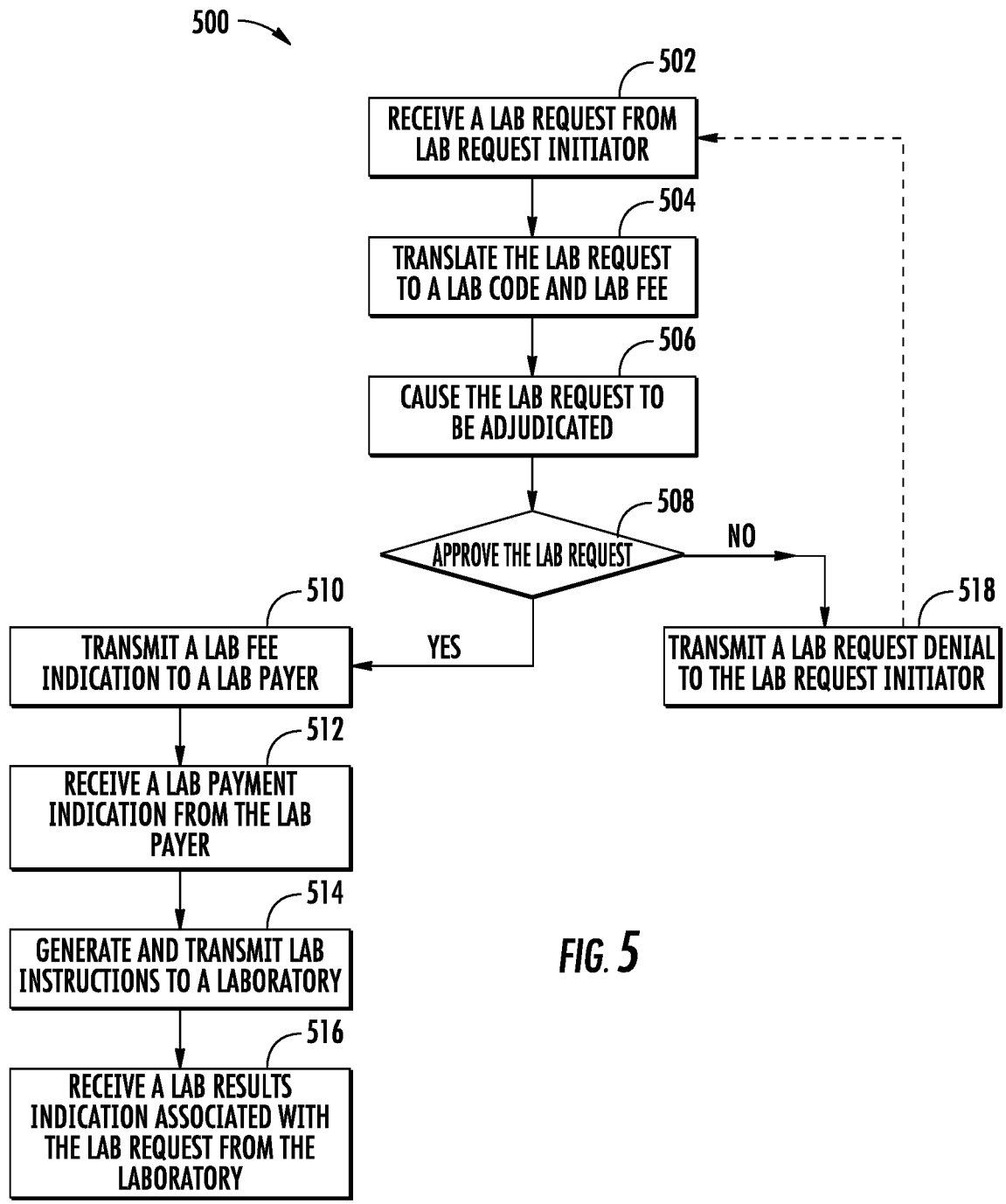
FIG. 5 illustrates a flow diagram of exemplary operations of a lab clearinghouse system in accordance with some embodiments discussed herein.

FIG. 5 illustrates a flow diagram of an example lab clearinghouse system for centralized management of medical tests, in accordance with some embodiments discussed herein.

The operations illustrated in FIG. 5 may, for example, be performed by, with the assistance of, and/or under the control of an apparatus 200, as described above. In this regard, performance of the operations may invoke one or more of processor 210, memory 220, input/output circuitry 240, communications circuitry 230, and/or lab clearinghouse circuitry 400 (e.g., context determination circuitry 414, analytical engine 416, and/or communications interface 418).

As shown in operation 502, the apparatus 200 includes means, such as processor 210, memory 220, input/output circuitry 240, communications circuitry 230, lab clearinghouse circuitry 400 (e.g., context determination circuitry 414, analytical engine 416, and/or communications interface 418), or the like, for receiving a lab request from a lab request initiator (502). For instance, input/output circuitry 240 may receive a lab request from a user while communications circuitry 208 may receive data from another device. In some embodiments, the lab request initiator may be a medical provider and may be specific to a single physician, a group of physicians, a hospital, or other collection of medical providers with the credentials to order medical testing of a patient or patient's specimen. The lab request may request the performance of one or more medical tests and may include various information relative to the medical tests, patient, lab request initiator, laboratory for performing the medical tests, etc.

In some embodiments, the lab clearinghouse device 120 and lab request initiator may communicate to generate the lab request prior to the lab clearinghouse device 120 receiving the lab request. The lab clearinghouse device 120 may present a series of questions to the lab request initiator. The answers of such questions may form the lab request.

Thereafter, as shown in operation 504, the apparatus 200 includes means, such as processor 210, memory 220, lab clearinghouse data store 300, lab clearinghouse circuitry 400 (e.g., context determination circuitry 414, analytical engine 416, and/or communications interface 418), or the like, for translating the lab request to a lab code associated with a lab fee (504). The lab request may be translated to a lab code by comparing the one or more medical tests requested in the lab request to a predetermined set of lab codes associated with the medical tests and correlating the medical tests to one or more lab codes. Each medical test may be associated with an individual or unique lab code or may be grouped together under an individual lab code. The lab codes are generally associated with lab fees and may be associated with a single lab fee or a range of lab fees. Translation of the lab request to the lab code may include calculating the appropriate lab code and lab fee based on the medical tests requested. Translation of the lab request to the lab code may consider any of the various information stored in the lab clearinghouse data store (e.g., patient data, physician data, provider data, laboratory data, payer data, or combinations thereof).

As shown in operation 506, the apparatus 200 includes means, such as processor 210, memory 220, lab clearinghouse data store 300, lab clearinghouse circuitry 400 (e.g., context determination circuitry 414, analytical engine 416, and/or communications interface 418), or the like, for causing the lab request to be adjudicated (506). The lab request may be adjudicated in real time. That is, after receipt of the lab request, the lab request may be adjudicated prior to transmitting lab instructions to a laboratory 110C for performance of the medical tests requested in the lab request. The lab clearinghouse device has access to a variety of information that may allow for adjudication of the lab request prior to performance of the medical tests requested in the lab request.

Adjudication of the lab request may be performed by the lab clearinghouse device 120 and/or the lab payer 110B. For instance, in some embodiments, both the lab clearinghouse device 120 and the lab payer 110B may communicate to adjudicate the lab request prior to performance of the medical tests requested in the lab request.

In some embodiments, adjudication of the lab request may be performed autonomously by the lab clearinghouse device 120. In such embodiments, the lab clearinghouse device 120 may analyze patient data, physician data, provider data, laboratory data, payer data, or combinations thereof; and determine a likelihood of payment by at least one lab payer of a plurality of lab payers by comparing the patient data, physician data, provider data, lab data, payer data, or combinations thereof to the lab request. The likelihood of payment by the at least one lab payer of the plurality of lab payers may be based on a pattern of activity established in the patient data, physician data, provider data, lab data, payer data, or combinations thereof.

In some embodiments, the pattern of activity established in the patient data, physician data, provider data, lab data, payer data, or combinations thereof may be based on a series of prior payments made by a patient, insurance carrier, or combinations thereof. For instance, the pattern of activity may establish a payment history of the insurance carrier over a series of prior payments made by the insurance carrier for the patient or for several patients. Such pattern of activity may be used to determine the likelihood of payment by the insurance carrier for future medical tests. In some embodiments, the pattern of activity may establish a payment history of the patient or member over a series of prior payments made by the patient or member, which similarly may be used to determine the likelihood of payment by the patient or member for future medical tests. The series of prior payments may be limited to certain prior medical tests or grouped together by similarity in medical tests to which they relate.

In some embodiments, the pattern of activity established in the patient data, physician data, provider data, lab data, payer data, or combinations thereof may be based on established procedures associated with a patient, lab payer, or combinations thereof. For instance, the pattern of activity may be based on policies of the insurance carrier that may distinguish certain medical tests which the insurance carrier may fully or partially reimburse. The pattern of activity may show how the established procedures are followed. Still further, in some embodiments, the pattern of activity may be based on prior medical tests, prior payments, established procedures, or combinations thereof. For instance, the pattern of activity may show that for the past several years, certain medical tests are fully or partially reimbursed by a lab payer or that certain medical tests are only fully or partially reimbursed by a lab payer when described in a certain fashion in accordance with an established procedure of the lab payer.

In some embodiments, the pattern of activity may be based on real time interactions with the lab request initiator and the lab clearinghouse device 120. For instance, the lab clearinghouse device 120 may communicate with the lab request initiator to generate the lab request. A series of questions may be presented to the lab request initiator from the lab clearinghouse device 120 to generate the lab request. The answers to the series of questions may form the pattern of activity that is then used to determine a likelihood of payment.

The lab clearinghouse device 120 may retrieve patient data, physician data, provider data, lab data, payer data, or combinations thereof from one or more external devices operated by one or more of a plurality of laboratories, medical providers, lab payers, or combinations thereof in adjudicating the lab request. To facilitate adjudication of the lab request, the lab clearinghouse device 120 may request and receive additional data needed in adjudicating the lab request. For instance, the lab clearinghouse device 120 may request and retrieve additional patient data (e.g., biographical data, diagnosis, etc.), lab data (e.g., which laboratory is requested), lab payer data (e.g., which insurance carrier(s) are implicated by the lab request), or any other data that may be needed in adjudicating the lab request.

In some embodiments, adjudication of the lab request may include translating the lab request to a lab request indication and providing the lab request indication to a lab payer, wherein the lab request indication is configured to allow the lab payer to determine a likelihood of approval of the lab request associated with the lab request indication. The lab request indication may be configured to allow the lab payer to determine a likelihood of approval of the lab request associated with the lab request indication by including relevant information (e.g., patient data, physician data, provider data, laboratory data, payer data, or combinations thereof) in the lab request indication such that the lab payer can determine whether the medical tests requested in the lab request would likely be paid for (or how much of the lab request would likely be paid for) by one or more lab payers. One or more lab payers may be involved (e.g., multiple insurance policies may be triggered by the medical tests, patients may be responsible for part or all of the medical tests, etc.). The lab payers may communicate with the lab clearinghouse device to adjudicate the lab requests.

As shown in operation 508, the apparatus 200 includes means, such as processor 210, memory 220, lab clearinghouse data store 300, lab clearinghouse circuitry 400 (e.g., context determination circuitry 414, analytical engine 416, and/or communications interface 418), or the like, for approving or denying the lab request based on adjudication of the lab request (508). In some embodiments, approving the lab request based on adjudication of the lab request may include generating and transmitting a lab fee indication to one lab payer of the plurality of lab payers, generating lab instructions associated with the lab request, and transmitting the lab instructions associated with the lab request to one laboratory of the plurality of medical laboratories for performance of the lab instructions. As shown in FIG. 5, the apparatus 200 includes means, such as processor 210, memory 220, input/output circuitry 240, communications circuitry 230, lab clearinghouse circuitry 400 (e.g., context determination circuitry 414, analytical engine 416, and/or communications interface 418), or the like, for transmitting a lab fee indication to a lab payer (510). As shown in FIG. 5, the apparatus 200 includes means, such as processor 210, memory 220, input/output circuitry 240, communications circuitry 230, lab clearinghouse circuitry 400 (e.g., context determination circuitry 414, analytical engine 416, and/or communications interface 418), or the like, for receiving a lab payment indication from the lab payer (512).

One or more lab payers 110B may receive the lab fee indication and a lab payment indication indicating that payment will be provided may be transmitted from one or more lab payers 110B. Lab payment may be transmitted at that time or at a later date. For example, in some embodiments, one or more insurance carriers may transmit a payment for the lab request and in some embodiments, a patient may be responsible for payment of part or all of the medical tests requested in the lab request. The patient may transmit a lab payment for the medical tests requested in the lab request.

The lab fee indication may be transmitted to a lab payer (e.g., an insurance carrier, patient, member, etc. via a client device or an intermediary device, such as a provider 110A) and lab payment may be transmitted from a lab payer (e.g., an insurance carrier, patient, member, etc. via a client device or an intermediary device, such as a provider 110A). For instance, a lab fee indication may be transmitted to a provider 110A which then provides the lab fee indication to the patient or member for payment. The lab fee indication may be transmitted to multiple lab payers and lab payment may be received from multiple lab payers.

The apparatus 200 includes means, such as processor 210, memory 220, lab clearinghouse circuitry 400 (e.g., context determination circuitry 414, analytical engine 416, and/or communications interface 418), or the like, for generating lab instructions for performance of one or more medical tests (514). The apparatus 200 includes means, such as processor 210, memory 220, input/output circuitry 240, communications circuitry 230, lab clearinghouse circuitry 400 (e.g., context determination circuitry 414, analytical engine 416, and/or communications interface 418), or the like, for transmitting lab instructions to a laboratory (514). Once the lab payment indication is received from one or more lab payers 110B, such that performance of the lab request is intended to be fully compensated for, the lab clearinghouse device 120 may generate lab instructions and transmit such instructions to one or more laboratories 110C. The lab instructions may specify certain medical tests to be performed, time and date of performance, conditions needed for performance of the medical tests (e.g., to avoid inaccurate testing, mishandling of specimens, or inconsistency across laboratories), and any other information that may enable the receiving laboratory 110C in performing the medical tests requested in the associated lab request. The lab instructions may be transmitted to a single laboratory 110C for performance of the one or more medical tests requested in the lab request. In some embodiments, the lab instructions may be transmitted to more than one laboratory 110C for performance of one or more medical tests requested in the lab request. The laboratory 110C to which lab instructions are transmitted may be determined by the lab request initiator. Each laboratory 110C may be instructed to perform a certain medical test or may be instructed that certain medical tests are needed and request confirmation of whether the medical tests can be performed. The lab clearinghouse device 120 may communicate with the laboratories 110C such that the medical tests requested in the lab request are performed.

The apparatus 200 includes means, such as processor 210, memory 220, input/output circuitry 240, communications circuitry 230, lab clearinghouse circuitry 400 (e.g., context determination circuitry 414, analytical engine 416, and/or communications interface 418), or the like, for receiving a lab results indication associated with the lab request from the laboratory (516). Once the medical tests are performed by the receiving laboratory 110C, the laboratory 110C may generate and transmit a lab results indication to the lab clearinghouse device 120. The lab results indication may indicate that lab results have been obtained and may list the lab results. The lab clearinghouse device 120 may then transmit the lab results indication with the lab results to one or more of the medical provider 110A and lab payer 110B associated with the lab request. In some embodiments, the lab clearinghouse device 120 may transmit the lab results indication with the lab results to the patient (via a client device) associated with the lab request using means such as input/output circuitry 240, communications circuitry 230. The lab clearinghouse device 120 may store the lab results indication and the lab results in apparatus 200, such as in the lab clearinghouse data store 300.

The laboratory 110C beneficially may not need to generate and submit insurance claims relating to the medical tests to a lab payer 110B. The laboratory 110C may communicate solely with the lab clearinghouse device 120 to transmit lab results indications and lab results and receive payment for performance of the medical tests. The laboratory 110C is thereby more likely to receive payment (as payment has already been received by the lab clearinghouse device 120 prior to instructing performance of the medical tests, or payment has already been approved by the lab payer, even if payment has not yet been transmitted) and as a result, utilization of the lab clearinghouse system can eliminate the administrative and overhead costs associated with generating and submitting claims and following-up to negotiate the terms of payment for performance of the medical tests.

The apparatus 200 includes means, such as processor 210, memory 220, input/output circuitry 240, communications circuitry 230, lab clearinghouse circuitry 400 (e.g., context determination circuitry 414, analytical engine 416, and/or communications interface 418), or the like, for generating and transmitting a lab request denial to the lab request initiator to revise the lab request or may deny the lab request without suggested revisions. As shown in FIG. 5, the method (500) may include transmitting a lab request denial to the lab request initiator (518). The lab request denial may indicate that the lab request needs to be revised and may include a suggested revised lab request. The suggested revised lab request may be generated by the lab clearinghouse device 120 to overcome problems that were found with the original lab request. That is, the suggested revised lab request may include one or more medical tests to replace one or more medical tests requested in the original lab request. After adjudicating the lab request, the lab clearinghouse device 120 may determine that other medical tests would have a higher likelihood of payment. The lab clearinghouse device has access to a variety of information (e.g., patient data, physician data, provider data, laboratory data, payer data, or combinations thereof) that may allow for providing suggested revised lab requests. The suggested revised lab request may include various information such as revised laboratories to perform the medical tests, revised deadlines, revised patient data, etc. that may alter the lab request such that it will be authorized for payment by the lab payer prior to performance of any medical tests stemming from the lab request. For example, the lab clearinghouse device 120 may determine that the medical tests may not be fully or partially paid for by the insurance carrier and suggest one or more different medical tests in the suggested revised lab requests that would likely be paid for by the insurance carrier.

The apparatus 200 may include means, such as processor 210, memory 220, input/output circuitry 240, communications circuitry 230, lab clearinghouse circuitry 400 (e.g., context determination circuitry 414, analytical engine 416, and/or communications interface 418), or the like, for receiving a revised lab request from the lab request initiator. The lab request initiator (e.g., medical provider 110A) may generate and transmit the revised lab request to the lab clearinghouse device 120. The revised lab request may include one or more medical tests to replace one or more medical tests requested in the original lab request. The revised lab request may include various information such as revised laboratories to perform the medical tests, revised deadlines, revised patient data, etc. that may enable the lab request to be paid by the lab payer prior to performance of any medical tests stemming from the lab request.

Receipt of the revised lab request may cause the method to return to operation 502, described above including receiving a lab request from the lab request initiator and then translating the revised lab request to a lab code and lab fee. The method (500) may then proceed through causing the revised lab request to be adjudicated and approving or denying the revised lab request. It will be appreciated that these operations are similar to the operations of receiving a lab request from the lab request initiator (502), translating the lab request to a lab code and lab fee (504), causing the lab request to be adjudicated (506), and approving or denying the lab request (508) as discussed above.

In some embodiments, the method 500 may include receiving the original lab request after transmitting the lab request denial. In some embodiments, instead of receiving a revised lab request, the original lab request may be resubmitted overriding the lab request denial. For instance, a provider, e.g., a physician, may determine that the original lab request should not have been denied and may resubmit the lab request without adjusting the content of the lab request. The method 500 may proceed directly to approving the original lab request or not (508), as discussed above.

Figure 6:
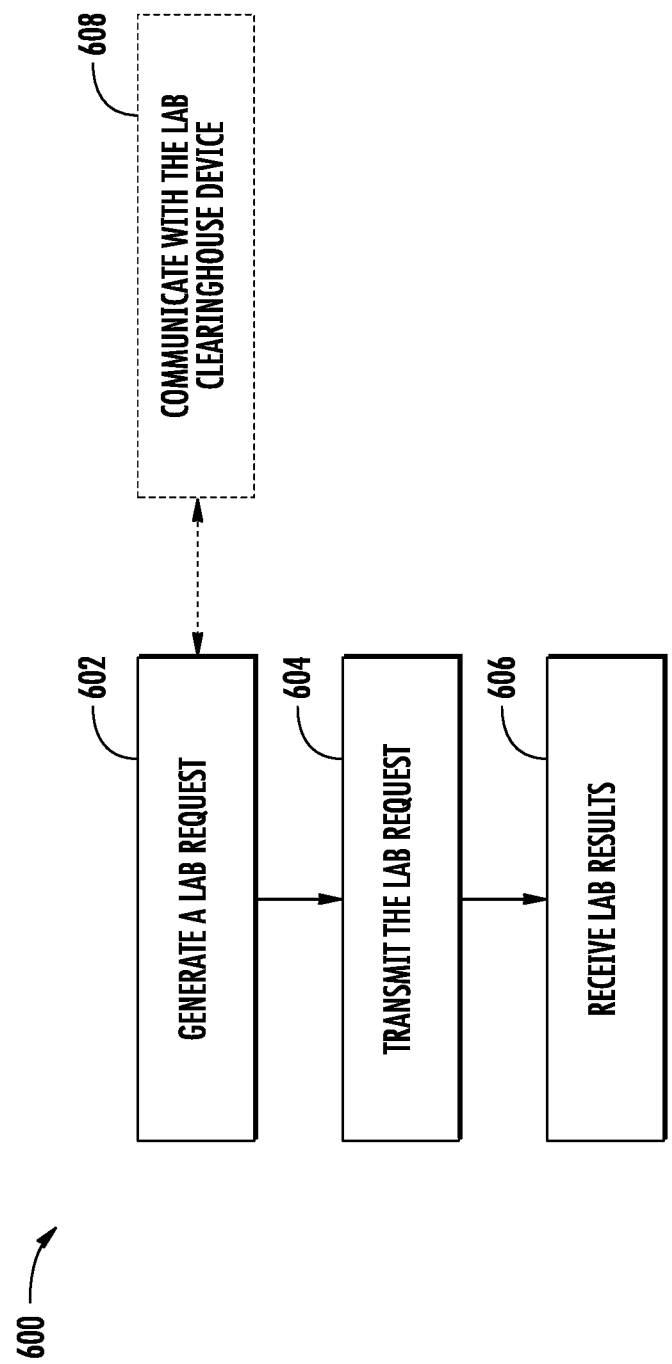
FIG. 6 illustrates a flow diagram of exemplary operations of a medical provider in accordance with some embodiments discussed herein.

FIG. 6 illustrates a flow diagram of exemplary operations of an example medical provider in accordance with some embodiments discussed herein. The operations illustrated in FIG. 6 may, for example, be performed by, with the assistance of, and/or under the control of an apparatus 200, as described above. In this regard, performance of the operations may invoke one or more of processor 210, memory 220, input/output circuitry 240, communications circuitry 230, lab clearinghouse circuitry 400 (e.g., context determination circuitry 414, analytical engine 416, and/or communications interface 418), or the like. The medical provider 110A may include means, such as processor 210, memory 220, input/output circuitry 240, communications circuitry 230, lab clearinghouse circuitry 400 (e.g., context determination circuitry 414, analytical engine 416, and/or communications interface 418), or the like for generating a lab request (602), transmitting a lab request to the lab clearinghouse device (604), and receiving lab results (606). For instance, the input/output circuitry and/or communications circuitry may transmit a lab request (604) and receive lab results (606). The processor 210, memory 220, lab clearinghouse circuitry 400 (e.g., context determination circuitry 414, analytical engine 416, and/or communications interface 418), or the like may generate a lab request (602). In some embodiments, the medical provider 110A may also include means, such as processor 210, memory 220, input/output circuitry 240, communications circuitry 230, lab clearinghouse circuitry 400 (e.g., context determination circuitry 414, analytical engine 416, and/or communications interface 418), or the like, for receiving a lab request denial, and generating and transmitting a revised lab request. The lab results may include all supporting documentation (e.g., genomic file).

In some embodiments, the medical provider 110A may include means, such as processor 210, memory 220, input/output circuitry 240, communications circuitry 230, lab clearinghouse circuitry 400 (e.g., context determination circuitry 414, analytical engine 416, and/or communications interface 418), or the like for communicating with the lab clearinghouse device (608) to generate the lab request (602). For instance, the lab clearinghouse device 120 and medical provider 110A may communicate to generate the lab request. The lab clearinghouse device 120 may present a series of questions to the lab request initiator. The answers of such questions may form the lab request. As shown in FIG. 6, operation 608 may entail back and forth communication between the medical provider 110A and the lab clearinghouse device 120.

Figure 7:
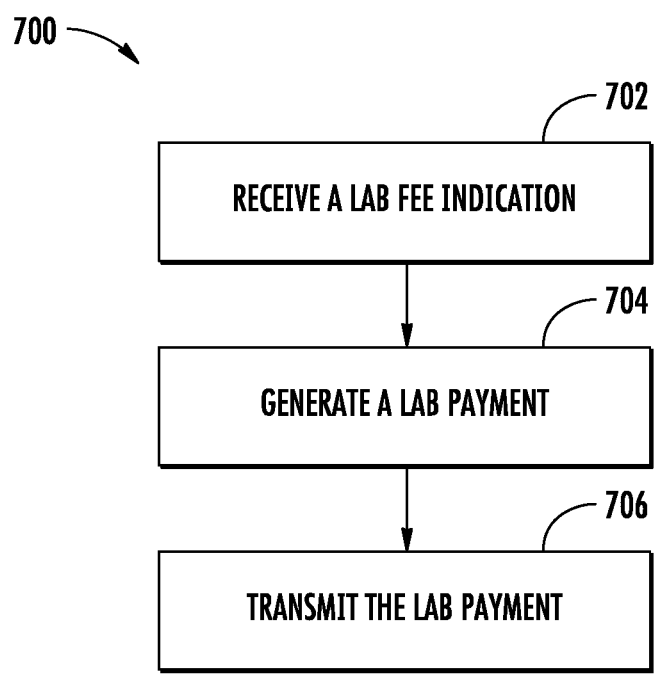
FIG. 7 illustrates a flow diagram of exemplary operations of a lab payer in accordance with some embodiments discussed herein.

FIG. 7 illustrates a flow diagram of exemplary operations of an example lab payer in accordance with some embodiments discussed herein. The operations illustrated in FIG. 7 may, for example, be performed by, with the assistance of, and/or under the control of an apparatus 200, as described above. In this regard, performance of the operations may invoke one or more of processor 210, memory 220, input/output circuitry 240, communications circuitry 230, lab clearinghouse circuitry 400 (e.g., context determination circuitry 414, analytical engine 416, and/or communications interface 418), or the like. The lab payer 110B may include means, such as a processor 210, memory 220, input/output circuitry 240, communications circuitry 230, lab clearinghouse circuitry 400 (e.g., context determination circuitry 414, analytical engine 416, and/or communications interface 418), or the like, for receiving a lab fee indication (702), generating a lab payment (704), and transmitting a lab payment (706). For instance, the input/output circuitry 240 and/or communications circuitry 230 may receive a lab fee indication, the processor 210 and/or memory 220 may generate a lab payment, and the input/output circuitry 240 and/or communications circuitry 230 may transmit a lab payment. In some embodiments, the lab payer 110B may also include means, such as a processor 210, memory 220, input/output circuitry 240, communications circuitry 230, lab clearinghouse circuitry 400 (e.g., context determination circuitry 414, analytical engine 416, and/or communications interface 418), or the like, for receiving a lab request indication and determining a likelihood of approval of the lab request associated with the lab request indication. For instance, the input/output circuitry 240 and/or communications circuitry 230 may receive a lab request indication and the processor 210 and/or memory 220 may determine a likelihood of approval of the lab request associated with the lab request indication. Receiving a lab request indication and determining a likelihood of approval of the lab request associated with the lab request indication may occur prior to receiving a lab fee indication (702).

Figure 8:
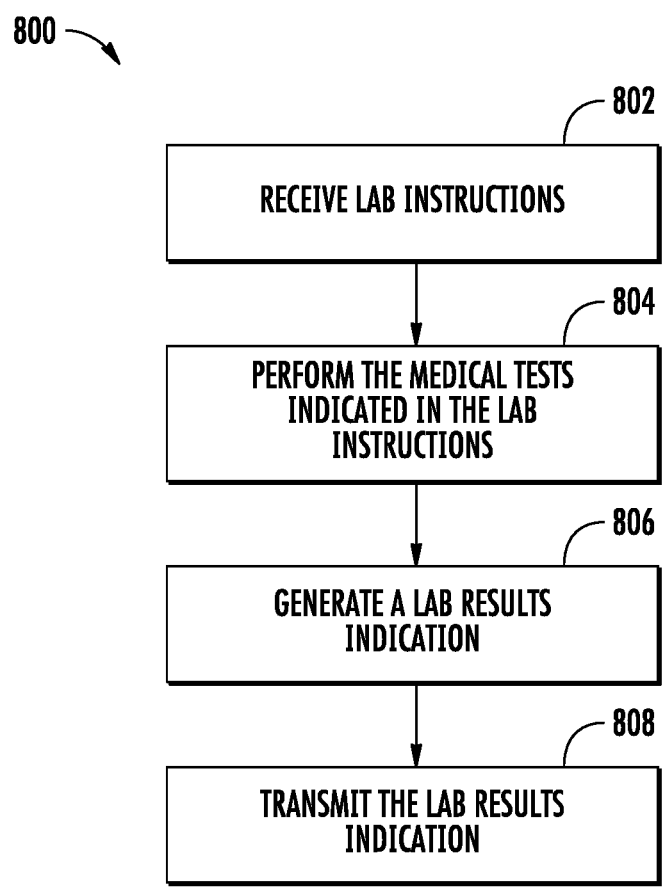
FIG. 8 illustrates a flow diagram of exemplary operations of a laboratory in accordance with some embodiments discussed herein.

FIG. 8 illustrates a flow diagram of exemplary operations of an example laboratory in accordance with some embodiments discussed herein. The operations illustrated in FIG. 8 may, for example, be performed by, with the assistance of, and/or under the control of an apparatus 200, as described above. In this regard, performance of the operations may invoke one or more of processor 210, memory 220, input/output circuitry 240, communications circuitry 230, lab clearinghouse circuitry 400 (e.g., context determination circuitry 414, analytical engine 416, and/or communications interface 418), or the like. The laboratory 110C may include means, such as processor 210, memory 220, input/output circuitry 240, communications circuitry 230, lab clearinghouse circuitry 400 (e.g., context determination circuitry 414, analytical engine 416, and/or communications interface 418), or the like, for receiving lab instructions (802), performing the medical tests indicated in the lab instructions (804), generating a lab results indication (806), and transmitting the lab results indication to the lab clearinghouse device (808). For instance, the input/output circuitry 240 and/or communications circuitry 230 may receive lab instructions, the processor 210 and/or memory 220 may perform the medical tests indicated in the lab instructions and/or generate a lab results indication, and the input/output circuitry 240 and/or communications circuitry 230 may transmit the lab results indication.

Provided herein are systems, methods, devices, and computer program products to manage lab requests and lab payments where the lab clearinghouse device is designed to be the intermediary in transmissions between patients, providers (e.g., physicians, hospitals, etc.), lab payers, and laboratories, and as a result, the lab clearinghouse device has access to information, e.g., electronic medical records, from each of these entities. The lab clearinghouse device may adjudicate the lab request in real-time based on information received from the provider, the member (e.g., patient), the lab payer, and any contract with the lab to perform the medical tests ordered in the lab request thereby eliminating the need for laboratories to create insurance claims for payment, or for lab payers to adjudicate such insurance claims. The lab clearinghouse device may generate and transmit a lab fee indication indicating that payment for one or more medical tests is needed, receive a payment indication indicating that payment will be provided, and generate lab instructions for performance of the medical tests. Through the use of a lab clearinghouse device as described herein, lab payers and laboratories may realize reduced costs and increased efficiency due to the removal of the need to create insurance claims, and lab payers, patients, and medical providers may have access to data (e.g., detailed and complex test results) through the lab clearinghouse device that may otherwise not be readily accessible.

By adjudicating the lab request prior to generating and transmitting lab instructions, liability is established and resolved prior to performance of the medical tests by the laboratory. Laboratories may thereby experience an increase in payments received and a concomitant decrease in the overhead associated with debt collection. Further, by translating the lab requests to lab codes associated with lab fees prior to performance of the medical tests and adjudicating the lab requests prior to performance of the medical tests, the lab clearinghouse device allows for shifting of the price structure away from claims-based payment adjudication that prices large groups of tests under broad claims to a model that prices medical tests based on the individual requirements of the medical tests themselves. Medical tests may be priced based on the underlying data regarding the lab request (e.g., patient, laboratory, etc.) rather than the insurance claim that results from a lab request. With this more granular pricing structure using lab codes and adjudicating lab requests, use of a lab clearinghouse device as described herein enables medical tests to be priced based on the actual needs of the patient. The lab request can thereby be adjudicated based on the needs of the patient and can be modified through lab request denials and suggested revised lab requests to obtain a lab request that is more likely to be paid while still meeting the needs of the patient. Denial of payment by insurance companies due to ineligible tests, clinical editing, duplicate tests, etc. can be avoided on the front end.

Through the use of a lab clearinghouse system employing the lab clearinghouse device, data from the provider, lab payer, and laboratories are centralized into a single lab clearinghouse device where the adjudication, approval/denial, generation of instructions, payments, and results processing take place. Accordingly, the lab clearinghouse device may allow for less strain on the systems of the medical providers, laboratories, and lab payers leading to increased system efficiency. Due to the removal of the need to create and submit claims, this effect is particularly amplified for laboratories and lab payers and may also allow for reduced network traffic and data processing in other entities (e.g., intermediary systems, collection agencies, and the like). Moreover, medical tests may be priced more specifically (rather than being grouped with 100's of other labs and priced with those other labs), thereby reducing costs for the lab payer and the patient (e.g., due to reduced denials). The lab clearinghouse device may also increase provider engagement as the provider communicates with the lab clearinghouse device to determine the lab request (e.g., through the generation and submission of suggested revised lab requests and revised lab requests).

Embodiments of the present invention have been described above with reference to block diagrams and flowchart illustrations of methods, devices, systems and computer program goods. It will be understood that each block of the circuit diagrams and process flowcharts, and combinations of blocks in the circuit diagrams and process flowcharts, respectively, can be implemented by various means including computer program instructions. These computer program instructions may be loaded onto a general purpose computer, special purpose computer, or other programmable data processing apparatus, such as processor 210, lab clearinghouse data store 300, and/or lab clearinghouse circuitry 400 (e.g., context determination circuitry 414, analytical engine 416, and/or communications interface 418) discussed above with reference to FIG. 2, to produce a machine, such that the computer program product includes the instructions which execute on the computer or other programmable data processing apparatus create a means for implementing the functions specified in the flowchart block or blocks.

These computer program instructions may also be stored in a computer-readable storage device (e.g., memory 220) that can direct a computer or other programmable data processing apparatus to function in a particular manner, such that the instructions stored in the computer-readable storage device produce an article of manufacture including computer-readable instructions for implementing the function discussed herein. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions discussed herein.

Accordingly, blocks of the block diagrams and flowchart illustrations support combinations of means for performing the specified functions, combinations of steps for performing the specified functions and program instruction means for performing the specified functions. It will also be understood that each block of the circuit diagrams and process flowcharts, and combinations of blocks in the circuit diagrams and process flowcharts, can be implemented by special purpose hardware-based computer systems that perform the specified functions or steps, or combinations of special purpose hardware and computer instructions.

Some embodiments of the present invention also use a second screen, as discussed herein. For instance, a first screen may be presented to a first user while a second screen may be presented to a second user of the lab clearinghouse system 100. The format of the display may appear differently to different users of the lab clearinghouse system 100. For instance, users may have particular preference for layouts or text fonts. The particular preferences may be considered when generating the communications and displays. The system may utilize any number of screens necessary for use of the lab clearinghouse system 100 in a meaningful way to each user of the system.

Many modifications and other embodiments of the inventions set forth herein will come to mind to one skilled in the art to which these embodiments of the invention pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. An intermediary computing device in electronic communication with a plurality of medical provider computing devices, a plurality of lab payer computing devices, a plurality of laboratory computing devices, and at least one lab payer computing device through one or more application programming interfaces (APIs), the intermediary device comprising a processor and a memory storing computer instructions that, when executed by the processor, cause the intermediary device to:
  receive, via an API, an electronic message, wherein the electronic message comprises a lab request originating from a lab request initiator associated with a medical provider of a plurality of medical providers;
  responsive to receiving the electronic message, automatically parse the electronic message to determine a context of the electronic message, wherein (a) the context of the message is determined based at least in part on a sending user identifier in the electronic message and an attachment in the electronic message, (b) the context of the message is a lab request originating from a lab request initiator associated with a medical provider of a plurality of medical providers, the lab request initiator being associated with at least one medical provider of the plurality of medical providers, (c) the lab request comprises (1) patient data, medical provider data, and lab data, (2) the patient data comprises one or more of patient name data, patient preference data, patient contact data, patient gender data, patient address data, patient birthdate data, or patient medical history data, (3) the medical provider data comprises one or more of lab location data or lab pricing data, (4) the lab request comprises a request for one or more medical tests to be performed, and (5) the lab request initiator operates a medical provider computing device of the plurality of medical provider computing devices;
  programmatically translate the lab request comprising the patient data, the medical provider data and the lab data to a lab code, wherein the lab code corresponds to lab fee associated with the lab code, and the lab code corresponds to the one or more medical tests;
  prior to transmitting the lab request to a laboratory computing entity for performance of the one or more medical tests, cause the lab request to be programmatically adjudicated, wherein programmatically adjudicating the lab request comprises:
    automatically generating and transmitting an API-based request for payment data,
    receiving an API-based response comprising the payment data, and
    adjudicating the lab request based at least in part on the patient data, the medical provider data, the lab data, and the payment data; and after adjudicating the lab request, approve, based at least in part on the adjudication, the lab request, wherein approving the lab request comprises:
generating and transmitting an API-based notification comprising the lab fee indication to the at least one lab payer computing device,
generating lab instructions associated with the lab request after the lab request has been adjudicated, and
transmitting, via an API, the lab instructions associated with the lab request to a laboratory computing device of the plurality of laboratory computing devices, wherein (a) the lab instructions comprise an indication to carry out the performance of the one or more corresponding medical tests, and (b) the lab instructions are displayed via an interface of the laboratory computing device of the plurality of laboratory computing devices.

2. The intermediary device of claim 1, wherein the computer instructions, when executed by the processor, cause the intermediary device to cause the lab request to be adjudicated by causing the intermediary device to:
determine a likelihood of payment by the at least one lab payer computing device by comparing the patient data, the medical provider data, the lab data, payment data, or combinations thereof to the lab request.

3. The intermediary device of claim 2, wherein the likelihood of payment by the at least one lab payer computing device is based at least in part on a pattern of activity established in the patient data, the medical provider data, the lab data, payment data, or combinations thereof.

4. The intermediary device of claim 3, wherein the pattern of activity established in the patient data, the medical provider data, the lab data, payment data, or combinations thereof is based at least in part on a series of prior medical tests associated with a patient, a physician, a medical provider, a laboratory, a payer, or combinations thereof.

5. The intermediary device of claim 3, wherein the pattern of activity established in patient data, the medical provider data, the lab data, payment data, or combinations thereof is based at least in part on a series of prior payments made by a patient, a payer, or combinations thereof.

6. The intermediary device of claim 3, wherein the pattern of activity established in patient data, the medical provider data, the lab data, payment data, or combinations thereof is based at least in part on established procedures associated with a patient, payer, or combinations thereof.

7. The intermediary device of claim 1, wherein a lab request denial comprises a suggested revised lab request.

8. The intermediary device of claim 1, wherein the computer instructions, when executed by the processor, further cause the intermediary device to transmit at least part of a lab payment.

9. The intermediary device of claim 8, wherein the computer instructions, when executed by the processor, further cause the intermediary device to transmit the lab results to the lab request initiator.

10. The intermediary device of claim 1, wherein the computer instructions, when executed by the processor, further cause the intermediary device to index data associated with the attachment in the electronic message to facilitate searching for the lab request or the attachment.

11. A method of providing centralized management through an intermediary computing device in electronic communication with a plurality of medical provider computing devices, a plurality of lab payer computing devices, a plurality of laboratory computing devices, and at least one lab payer computing device through one or more application programming interfaces (APIs), the method comprising:
receive, by intermediary computing device and via an API, an electronic message, wherein the electronic message comprises a lab request originating from a lab request initiator associated with a medical provider of a plurality of medical providers;
responsive to receiving the electronic message, automatically parsing, by intermediary computing device, the electronic message to determine a context of the electronic message, wherein (a) the context of the message is determined based at least in part on a sending user identifier in the electronic message and an attachment in the electronic message, (b) the context of the message is a lab request originating from a lab request initiator associated with a medical provider of a plurality of medical providers, the lab request initiator being associated with at least one medical provider of the plurality of medical providers, (c) the lab request comprises (1) patient data, medical provider data, and lab data, (2) the patient data comprises one or more of patient name data, patient preference data, patient contact data, patient gender data, patient address data, patient birthdate data, or patient medical history data, (3) the medical provider data comprises one or more of lab location data or lab pricing data, (4) the lab request comprises a request for one or more medical tests to be performed, and (5) the lab request initiator operates a medical provider computing device of the plurality of medical provider computing devices;
programmatically translating, by intermediary computing device, the lab request comprising the patient data, the medical provider data and the lab data to a lab code, wherein the lab code corresponds to lab fee associated with the lab code, and the lab code corresponds to the one or more medical tests;
prior to transmitting the lab request to a laboratory computing entity for performance of the one or more medical tests, causing the lab request to be programmatically adjudicated, wherein programmatically adjudicating the lab request comprises:
automatically generating and transmitting an API-based request for payment data,
receiving an API-based response comprising the payment data, and
adjudicating the lab request based at least in part on the patient data, the medical provider data, the lab data, and the payment data; and
after adjudicating the lab request, approving, by the intermediary computing device and based at least in part on the adjudication, the lab request, wherein approving the lab request comprises:
generating and transmitting an API-based notification comprising the lab fee indication to the at least one lab payer computing device,
generating lab instructions associated with the lab request after the lab request has been adjudicated, and
transmitting, via an API, the lab instructions associated with the lab request to a laboratory computing device of the plurality of laboratory computing devices, wherein (a) the lab instructions comprise an indication to carry out the performance of the one or more corresponding medical tests, and (b) the lab instructions are displayed via an interface of the laboratory computing device of the plurality of laboratory computing devices.

12. The method of claim 11, wherein causing the lab request to be adjudicated comprises:
   determining a likelihood of payment by the at least one lab payer computing device by comparing the patient data, the medical provider data, the lab data, payment data, or combinations thereof to the lab request.

13. The method of claim 11, wherein the likelihood of payment by the at least one lab payer computing device is based at least in part on a pattern of activity established in the patient data, the medical provider data, the lab data, payment data, or combinations thereof.

14. The method of claim 13, wherein the pattern of activity established in the patient data, the medical provider data, the lab data, payment data, or combinations thereof is based at least in part on a series of prior medical tests associated with a patient, a physician, a medical provider, a laboratory, a payer, or combinations thereof.

15. The method of claim 13, wherein the pattern of activity established in patient data, the medical provider data, the lab data, payment data, or combinations thereof is based at least in part on a series of prior payments made by a patient, a payer, or combinations thereof.

16. The method of claim 13, wherein the pattern of activity established in patient data, the medical provider data, the lab data, payment data, or combinations thereof is based at least in part on established procedures associated with a patient, payer, or combinations thereof.

17. A computer program product comprising a non-transitory computer readable medium having computer program instructions stored therein, said computer program instructions when executed by a processor of an intermediary computing device in electronic communication with a plurality of medical provider computing devices, a plurality of lab payer computing devices, a plurality of laboratory computing devices, and at least one lab payer computing device through one or more application programming interfaces (APIs), cause the computer program product to:
   receive, via an API, an electronic message, wherein the electronic message comprises a lab request originating from a lab request initiator associated with a medical provider of a plurality of medical providers;
   responsive to receiving the electronic message, automatically parse the electronic message to determine a context of the electronic message, wherein (a) the context of the message is determined based at least in part on a sending user identifier in the electronic message and an attachment in the electronic message, (b) the context of the message is a lab request originating from a lab request initiator associated with a medical provider of a plurality of medical providers, the lab request initiator being associated with at least one medical provider of the plurality of medical providers, (c) the lab request comprises (1) patient data, medical provider data, and lab data, (2) the patient data comprises one or more of patient name data, patient preference data, patient contact data, patient gender data, patient address data, patient birthdate data, or patient medical history data, (3) the medical provider data comprises one or more of lab location data or lab pricing data, (4) the lab request comprises a request for one or more medical tests to be performed, and (5) the lab request initiator operates a medical provider computing device of the plurality of medical provider computing devices;
   programmatically translate the lab request comprising the patient data, the medical provider data and the lab data to a lab code, wherein the lab code corresponds to lab fee associated with the lab code, and the lab code corresponds to the one or more medical tests;
   prior to transmitting the lab request to a laboratory computing entity for performance of the one or more medical tests, cause the lab request to be programmatically adjudicated, wherein programmatically adjudicating the lab request comprises:
   automatically generating and transmitting an API-based request for payment data,
      receiving an API-based response comprising the payment data, and
      adjudicating the lab request based at least in part on the patient data, the medical provider data, the lab data, and the payment data; and
   after adjudicating the lab request, approve, based at least in part on the adjudication, the lab request, wherein approving the lab request comprises:
      generating and transmitting an API-based notification comprising the lab fee indication to the at least one lab payer computing device,
      generating lab instructions associated with the lab request after the lab request has been adjudicated, and
      transmitting, via an API, the lab instructions associated with the lab request to a laboratory computing device of the plurality of laboratory computing devices, wherein (a) the lab instructions comprise an indication to carry out the performance of the one or more corresponding medical tests, and (b) the lab instructions are displayed via an interface of the laboratory computing device of the plurality of laboratory computing devices.

\* \* \* \* \*